United States Patent [19]

Miller et al.

[11] Patent Number: 5,770,598
[45] Date of Patent: Jun. 23, 1998

[54] HETEROCYCLIC COMPOUNDS

[75] Inventors: David D. Miller, Stevenage; Paul Barraclough, Loose; Sadie Vile; Ann L. Walker, both of Stevenage; Patrick V. R. Shannon, Penarth, all of United Kingdom; Laddawan Chunchatprasert, Khon, Thailand; Pierre P. M. Debont, Canterbury; Alan T. Hudson, Otford, both of United Kingdom

[73] Assignee: University College Cardiff Consultants Limited, United Kingdom

[21] Appl. No.: 765,227

[22] PCT Filed: Jul. 6, 1995

[86] PCT No.: PCT/GB95/01598

§ 371 Date: Apr. 10, 1997

§ 102(e) Date: Apr. 10, 1997

[87] PCT Pub. No.: WO96/01827

PCT Pub. Date: Jan. 25, 1996

[30] Foreign Application Priority Data

Jul. 7, 1994 [GB] United Kingdom ............... 9413758

[51] Int. Cl.$^6$ ............ A61K 31/41; C07D 491/048; C07D 495/04; C07D 487/04

[52] U.S. Cl. ............ 514/232.8; 514/321; 514/338; 514/364; 514/374; 514/381; 544/138; 546/199; 546/269.4; 548/131; 548/143; 548/238; 548/252

[58] Field of Search ............ 548/131, 143, 548/252, 421, 238; 544/138; 546/199, 269.4; 514/232.8, 321, 338, 364, 374, 381

[56] References Cited

U.S. PATENT DOCUMENTS 5,679,694 10/1997 Franzmann et al. ............ 514/339

FOREIGN PATENT DOCUMENTS 447703 9/1991 European Pat. Off. ............ 548/421
94/02483 2/1994 WIPO .

*Primary Examiner*—Fiona T. Powers
*Attorney, Agent, or Firm*—Nixon & Vanderhye

[57] ABSTRACT

The present invention relates to heterocyclic compounds which have been found to have anti-tumour activity. More specifically, the invention concerns Pyrrolo [3,2-b] carbazoles, 1H-Benzofuro [3,2-f] indoles and 1H-[1] Benzothieno [2,3-f] indoles, methods for their preparation, pharmaceutical formulations containing them and their use as anti-tumour agents.

7 Claims, No Drawings

HETEROCYCLIC COMPOUNDS

This is a National Stage application of PCT/GB95/01,599 filed Jul. 6, 1995.

The present invention relates to heterocyclic compounds which have been found to have anti-tumour activity. More specifically, the invention concerns Pyrrolo [3,2-b] carbazoles, Pyrrolo[2,3-b] carbazoles, 1H-Benzofuro [2,3-ƒ] indoles, 1H-Benzofuro [3,2-ƒ] indoles, 1H-[1] Benzothieno [2,3-ƒ] indoles and 1H-[1]Benzothieno [3,2-ƒ] indoles, methods for their preparation, pharmaceutical formulations containing them and their use as anti-tumour agents.

Research in the area of cancer chemotherapy has produced a variety of anti-tumour agents which have differing degrees of efficacy. Standard clinically used agents include adriamycin, actinomycin D, methotrexate, 5-fluorouracil, cis-platinum, vincristine and vinblastine. However, these presently available anti-tumour agents are known to have various disadvantages, such as toxicity to healthy cells and resistance to certain tumour types. There thus exists a continuing need to develop new and improved anti-tumour agents.

Khoshtariya et al disclose the synthesis of certain indolobenzo[b] thiophenes and certain indolobenzo[b] furans, khim. Geterotsikl. Soedin (1980), (2) 203–8, and khim Geterotsikl Soedin (1984), (10) 1366–70 respectively.

Kakhabrishvili et al, khim Geterotsikl Soedin (1985), (3) 355–8 disclose the synthesis of certain derivatives of indolo [5,6-d] and indolo [5,4-d] benzo[b] furans EP447,703 discloses the synthesis of certain benzo[5,6-b]benzofuran-2-carboxylates.

L.Chunchatprasert et al, J.Chem.Soc., Perkin Trans I, 1779 (1992) disclose the synthesis of pyrrolo[3,2-b] carbazoles, 1H-benzofuro[3,2-ƒ]indoles and 1H-[1] benzothieno[2,3-ƒindoles.

PCT application WO93/01512 discloses certain pyrrolo [3,2-b]carbazoles, pyrrolo[2,3-b]carbazoles 1H-benzofuro-[3,2-ƒ]indoles and 1H-(1) benzothieno [2,3-ƒ]indoles.

There have now been discovered novel compounds which exhibit anti-tumour cell activity with low toxicity against normal cell lines.

Thus, in a first aspect the present invention provides a compound of the general formula (I)

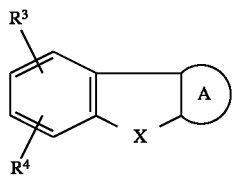

and salts and physiologically functional derivatives thereof,
wherein A) is

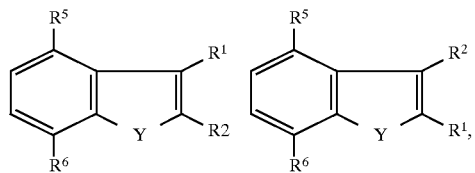

-continued

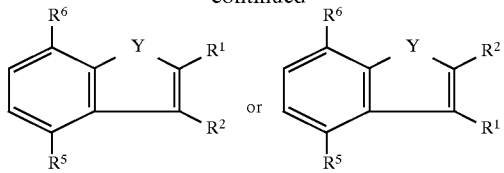

X is O, S, SO, $SO_2$, $CH_2$, CO or $NR^7$, wherein $R^7$ is H or the following groups which may be optionally substituted: cycoalkyl, cycloalkenyl, alkyl, alkenyl, alkynyl, aryl, aralkyl, acyl, aroyl, alkylsulphonyl or arylsulphonyl;

Y is O, S, SO, $SO_2$, $CH_2$, CO or $NR^7$;

$R^1$ is an optionally substituted 5- or 6-membered heterocyclic ring containing 1 to 4 heteroatoms wherein the 5- or 6- membered ring may be aromatic or non-aromatic.

$R^2$ is H, hydroxy, halo, haloalkyl, cyano, alkyl, aryl, alkenyl, alkynyl, alkoxy, (wherein alkyl, aryl, alkenyl, alkynyl, and alkoxy can be substituted), CHO, $COR^8$, $COOR^8$ wherein $R^8$ is hydrogen or is a $C_{1-10}$ optionally substituted hydrocarbyl group which may contain one or two oxygen atoms;

$R^3$ and $R^4$ are independently H, hydroxy, alkyl, haloalkyl, azido, CHO, $COR^8$, $CO_2R^8$, $CONHR^8$, $CONR^8R^9$, alkoxy, halo, cyano, nitro, amino, alkyl amino, dialkyl amino, carboxyl wherein $R^9$ is alkyl, aryl or aralkyl.

$R^5$ is H, hydroxy, nitro, amino, halo, cyano, CHO, $COR^8$, or the following groups which may be optionally substituted: alkyl, aryl, aryloxy, aralkyloxy, alkoxy, aralkyl.

$R^6$ is H, hydroxy, amino, nitro, halo, CHO, $COR^{10}$, $CO_2R^{10}$ wherein $R^{10}$ is optionally substituted alkyl or aryl, or $R^6$ is alkyl, aralkyl, or aryl wherein alkyl, aralkyl or aryl may be optionally substituted.

Suitably X is O, S, SO, $SO_2$, $CH_2$, CO or $NR^7$ wherein $R^7$ is suitably H, alkyl, aralkyl, aryl, alkenyl, acyl, alkynyl or optionally substituted sulphonyl;

Suitably $R^1$ is an optionally substituted five or six-membered heterocyclic ring containing one or two nitrogen atoms and optionally one other heteroatom.

Suitably $R^2$ is H, alkyl or $COOR^8$ wherein $R^8$ is as defined above;

Suitably $R^3$ and $R^4$ are independently H, hydroxy, alkyl, haloalkyl, alkoxy, halo, cyano, nitro, amino, alkylamino, dialkylamino or substituted alkyl;, Suitably $R^5$ is H, alkyl, substituted alkyl, aryl, aralkyl, nitro, halo, cyano or CHO;

Suitably $R^6$ is H, alkyl, aralkyl, nitro, halo, CHO or $COR^{10}$ wherein $R^{10}$ is suitably alkyl or aryl.

Alkyl groups may be straight or branched chain alkyl groups, and may contain 1–10 carbon atoms and suitably 1–6 carbon atoms. Examples of such alkyl groups include methyl, ethyl, t-butyl and the like.

Alkenyl groups may be straight or branched chain alkenyl groups, and may contain 2–10 carbon atoms and suitably 2–6 carbon atoms. Examples of such alkenyl groups include ethenyl, butenyl and the like.

Alkynyl groups may be straight or branched chain alkynyl groups, and may contain 2–10 carbon atoms and suitably 2–6 carbon atoms. Examples of such alkynyl groups include ethynyl, propynyl and the like.

Haloalkyl groups may be straight or branched chain haloalkyl groups and may contain 1–10 carbon atoms and suitably 1–6 carbon atoms. Such groups may contain one or more halo atoms. Examples of haloalkyl groups include trifluoromethyl, and the like.

Acyl groups are derived from carboxylic acids and may be straight or branched and may contain 1–10 carbon atoms and suitably 1–6 carbon atoms. Examples of suitable acyl groups include ethanoyl and propanoyl groups.

Alkoxy may be straight or branched and may contain 1–10 carbon atoms and suitably 1–6 carbon atoms. Examples of suitable alkoxy groups include methoxy, ethoxy and the like. Aryl includes both carbocyclic aryl groups and heterocyclic aryl groups normally containing a maximum of 10 ring atoms. Carbocyclic aryl groups include, eg phenyl and naphthyl and contain at least one aromatic ring. Heterocyclic aryl groups include eg thienyl, furyl, pyridyl, indolyl and quinolinyl rings.

An aralkyl group may contain from 1 to 4 atoms in the alkyl portion and the aryl portion may be a carbocyclic or heterocyclic aryl group.

A $C_{1-10}$ hydrocarbyl group optionally containing one or two oxygen atoms includes alkyl, hydroxyalkyl, alkenyl, alkynyl, $C_{1-10}$ carbamoylalkyl, $C_{1-10}$ alkoxyalkyl, cycloalkyl, cycloalkenyl, aralkyl, $C_{1-10}$ aryloxyalkyl, acyl or aryl. It may be optionally substituted by hydroxy, azido, alkenyl, halo, nitro, amino, (optionally substituted by one or 2 alkyl groups), cyano, carboxylate, alkyl ester, aralkyl ester, aryl ester (wherein the alkyl ester, aralkyl ester and aryl ester can be substituted) alkyl, aryl, aralkyl, aryloxy, arylalkoxy, substituted arylalkoxy, sulphinyl, sulphonyl, thio, $C_{1-10}$ alkylthio, alkoxy, hydroxyalkyl, haloalkyl, phosphate, phosphonate, silyl, silyloxy, (wherein silyl and silyloxy may be substituted by one or more $C_{1-6}$ alkyl or aryl groups) keto or, formyl.

Cycloalkyl includes both cycloalkyl groups and heterocycloalkyl groups normally containing between 3 and 6 ring atoms. Heterocycloalkyl groups include e.g. morpholino, thiomorpholino, piperidino, imidazolino, imidazolidino, pyrrolidino, pyrazolidino, piperazino, tetrahydrofuranyl, tetrahydropyranyl.

Cycloalkenyl includes both cycloalkenyl groups and heterocyclcoalkenyl groups normally containing between 3 and 6 ring atoms.

Substituents which may be present on alkyl esters, aralkyl esters and aryl esters include nitro, amino, hydroxy, alkoxy, halogen, cyano or alkyl.

Examples of suitable aromatic 5- or 6-membered rings containing 1 to 4 heteroatoms, include oxadiazole, oxazole, isoxazole, imidazole, pyrazole, triazole, tetrazole, pyrimidine, pyrazine, pyridazine, triazine, thiadiazole, thiazole, isothiazole.

Examples of suitable non-aromatic 5- or 6- membered rings containing 1 to 4 heteroatoms, include oxazoline, oxazolidine, thiazoline, thiazolidine, oxazolidinone, thiazolidinone, imidazoline, imidazolidine, pyrazolidine and pyrazoline.

Substituents which may be present on $R^1$ include azido, nitro, cyano, halo, haloalkyl, hydroxy, CHO, $COR^8$ $CO_2R^8$, $CONHR^8$, $CONR^8R^9$, oxo or the following groups which may be optionally substituted: alkyl, alkenyl, alkynyl, cycloalkyl, cycloalkenyl, aryl, aralkyl, heteroaryl, acyl, aroyl, aralkoyl, alkoxy or amino.

Substituents which may be present on the cycloalkyl, cycloalkenyl, alkyl, alkenyl, alkynyl, alkoxy, aryl, aralkyl, acyl, aroyl, alkylsulphonyl or arylsulphonyl groups include alkyl, alkoxy, halo, sulphinyl, hydroxy, amino (optionally substituted by one or two alkyl groups or part of a heterocyclic ring), haloalkyl (eg trifluoromethyl), sulphonyl, cyano, nitro or azido.

Substituents which may be present on the sulphonyl and sulphinyl include alkyl, aryl and aralkyl.

Halo represents fluoro, chloro, bromo or iodo.

Preferred compounds of formula (I), as defined above are those where

X preferably represents S or NH,

A) is preferably

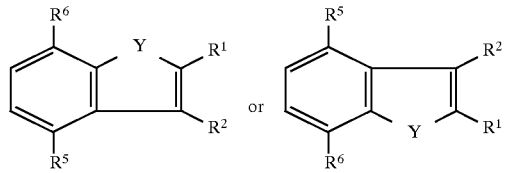

and Y preferably represents NH.

$R^1$ is preferably an optionally subsituted five-membered ring containing two nitrogen atoms and one oxygen atom wherein the 5-membered ring may be aromatic or non-aromatic. Preferred substituents are alkyl, aryl or aralkyl;

$R^2$ is preferably H or $C_{1-14}$ alkyl;

$R^3$ is preferably H, alkoxy, halo or hydroxy;

$R^4$ is preferably H, alkoxy, halo or hydroxy;

$R^5$ is preferably H or alkyl; and $R^6$ is preferably H or alkyl;

and salts and physiologically functional derivatives thereof.

Particularly preferred compounds according to the present invention include:

3,4-Dimethyl-2-(3-ethyl-1,2,4-oxadiazol-5-yl) pyrrolo[3,2-b]carbazole;

2-(3 -Benzyl-1,2,4-oxadiazol-5-yl)-3,4-dimethylpyrrolo[3,2-b]carbazole;

3,4-Dimethyl-2-(3-ethyl-1,2,4-oxadiazol-5-yl) pyrrolo[2,3-b]carbazole;

2-(3-ethyl-1,2,4-oxadiazol-5-yl)-4-methyl-1H-[1] benzothieno[2,3-ƒ]indole;

3,4-Dimethyl-2-(2-methyl-1,3,4-oxadiazol-5 -yl)-pyrrolo[3,2-b]carbazole;

3,4-Dimethyl-2-(2-ethyl-1,3,4-oxadiazol-5-yl)-pyrrolo[3,2-b]carbazole;

3,4-Dimethyl-2-(2-phenyl-1,3,4-oxadiazol-5-yl)-pyrrolo[3,2-b]carbazole;

2-(2-Ethyl-1,3,4-oxadiazol-5-yl)-4-methyl-1H-[1] benzothieno[2,3-ƒ]indole;

3,4-Dimethyl-2-[3-(3,4-methylenedioxyphenyl)-1,2,4-oxadiazol-5-yl]pyrrolo[3,2-b]carbazole;

4-Methyl-2-(2-oxazolin-2-yl)-1H-[1]benzothieno[2,3-ƒ]indole 3,4-Dimethyl-2-(3-methyl-1,2,4-oxadiazol-5-yl)pyrrolo[3,2-b]carbazole 3,4-Dimethyl-2-(3-methyl-1,2,4-oxadiazol-5-yl)pyrrolo[2,3-b]carbazole 3,4-Dimethyl-2-[(3-phenyl)-1,2,4-oxadiazol-5-yl]pyrrolo[3,2-b]carbazole 3,4-Dimethyl-2-(2-oxazolin-2-yl)pyrrolo[3,2-b]carbazole 3,4-Dimethyl-2-[3-(1-piperidinylmethyl)-1,2,4-oxadiazol-5-yl]pyrrolo[3,2-b]carbazole 3,4-Dimethyl-2-[3-(4-pyridyl)-1,2,4-oxadiazol-5-yl]pyrrolo[3,2-b]carbazole 3,4-Dimethyl-2-(3-methoxymethyl-1,2,4-oxadiazol-5-yl) pyrrolo[3,2-b]carbazole 3,4-Dimethyl-2-[3-(2-hydroxyethyl)-1,2,4-oxadiazol-5-yl] pyrrolo[3,2-b]carbazole 2-(3-Ethyl-1,2,4-oxadiazol-5-yl)-4-methyl-1H-[1]benzofuro[2,3f]indole
3,4-Dimethyl-2-(4,4-dimethyl-2-oxazolin-2-yl)pyrrolo[3,2-b]carbazole
3,4-Dimethyl-2-[3-(3-hydroxyphenyl)-1,2,4-oxadiazol-5-yl]pyrrolo[3,2-oxadiazol-5-yl]pyrrolo[3,2-b]carbazole
3,4-Dimethyl-2-[3-(N,N-dimethylaminomethyl)-1,2,4-oxadiazol-5-yl]pyrrolo[3,2-b]carbazole
3,4-Dimethyl-2-(tetrazol-5-yl)pyrrolo[3,2-b]carbazole)
3,4-Dimethyl-2-[3-(4-morpholinomethyl)-1,2,4-oxadiazol-5-yl]pyrrolo[3,2-b]carbazole
3,4-Dimethyl-2-(3-methoxyethyl-1,2,4-oxadiazol-5-yl)pyrrolo[3,2-b]carbazole
3,4-Dimethyl-2-(1,2,4-oxadiazol-5-yl)pyrrolo[3,2-b]carbazole and salts and physiologically functional derivatives thereof Compounds of the formula (I) wherein $R^1$ is a 1,2,4-oxadiazole ring can be made by reaction of a compound of the formula (II)

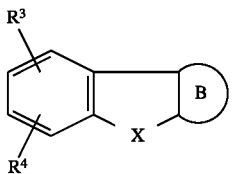

(II)

wherein B) is

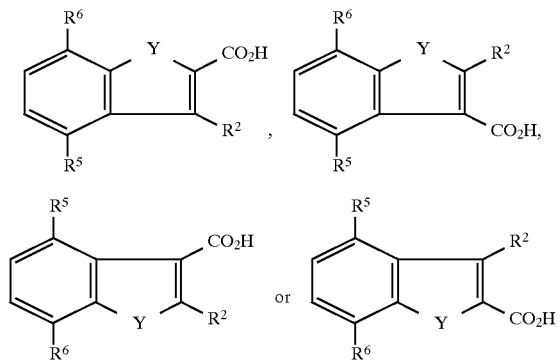

wherein X, Y, $R^2$, $R^3$, $R^4$, $R^5$ and $R^6$ are as defined above (with the proviso that $R^3$, $R^4$, $R^5$ and $R^6$ are not $NH_2$ or $CO_2R^8$. Amines at $R^3$, $R^4$, $R^5$ and $R^6$ must be suitably protected and esters can be obtained by modification of an appropriate group, eg CHO at $R^3$, $R^4$, $R^5$ and $R^6$ after the oxadiazole is formed), with carbonyl diimidazole in, for example, tetrahydrofuran, followed by reaction with the required amidoximes pretreated with sodium hydride and molecular sieves, at a temperature between 0° C. and 150° C. (see Comprehensive Heterocyclic Chemistry Ed. A. R. Katritzky and C. W. Rees, Pergamon Press, Oxford 1984).

Compounds of the formula (I) wherein $R^1$ is a 1,3,4-oxadiazole ring can be made by reaction of a compound of the formula (IIa)

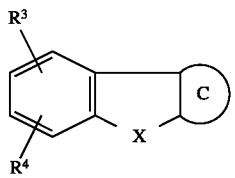

(IIa)

wherein C) is

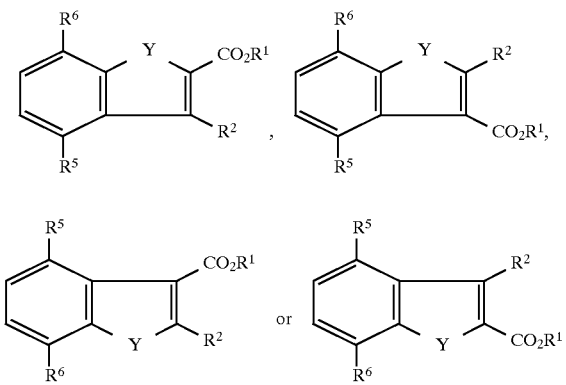

wherein X, Y, $R^3$, $R^4$, $R^5$ and $R^6$ are as defined above (with the proviso that $R^2$, $R^3$, $R^4$ and $R^5$ are not CHO, $COR^8$ or $CO_2R^8$ and $R^6$ is not CHO, $COR^{10}$ or $CO_2R^{10}$. Such groups may be introduced via eg formylation and subsequent modification after the oxadiazole is formed) and $R^{11}$ is an alkyl group, for example ethyl, with hydrazine hydrate to produce the hydrazide, this then being reacted with an ortho ester in a suitable solvent at a temperature between 0° C. and 150° C.

Compounds of the formula (II) can be produced from compounds of the formula (IIa) wherein $R^{11}$ aralkyl or alkyl. For example by catalytic hydrogenation e.g. in the presence of a palladium catalyst or by hydrolysis, e.g. in the presence of a base such as caesium carbonate, with the proviso that when $R^{11}$ is alkyl $R^8$ in $CO_2R^8$ is not alkyl and that when $R^{11}$ is aralkyl $R^8$ in $CO_2R^8$, is not aralkyl.

Compounds of the formula (IIa) may be produced in accordance with scheme 1 by reaction of a compound of the formula (III) with a compound of the formula (IV) in the presence of an acid catalyst as described in L. Chunchatprasert et al J.Chem.Soc, Perkin I, 1779 (1992).

Scheme 1

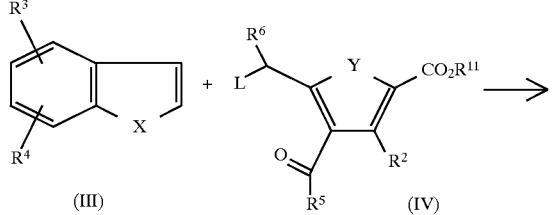

(III)        (IV)

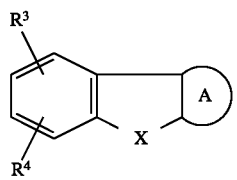

wherein A) is

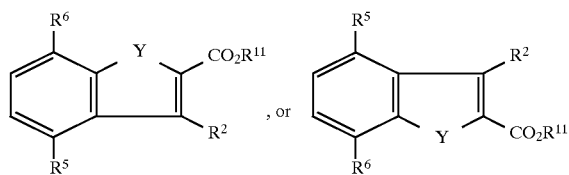

wherein L is a leaving group e.g. OCOCH$_3$,N$^+$Me, alkoxy, fluoroalkoxy, or halo, R$^{11}$ is alkyl or aralkyl e.g. Ethyl or benzyl and R$^2$, R$^3$, R$^4$, R$^5$, R$^6$, X and Y are as defined herein, with the proviso that R$^3$ and R$^4$ are not NH$_2$ (such compounds may be produced by reduction of compounds of formula (I) in which R$^3$ and R$^4$ are NO$_2$) and R$^5$ and R$^6$ are H, alkyl, aryl or aralkyl. Compounds of formula IIa in which R$^5$ and R$^6$ are OH, NO$_2$, NH$_2$, halo or CHO or R$^5$ is COR$^8$, or R$^6$ is COR$^{10}$ or CO$_2$R$^{10}$ may be prepared from compounds of formula IIa in which R$^5$ or R$^6$ are H by appropriate electrophilic substitution reactions with further modifications where required (J. March, Advanced Organic Chemistry Ed III Chapter 11, Wiley Interscience 1985).

Compounds of the formula (I) wherein R$^1$ is 1,2,4-oxadiazole or a 1,3,4-oxadiazole ring can also be produced in accordance with scheme 1 a by reaction of a compound of the formula (III) with a compound of the formula (IVa) in the presence of an acid catalyst.

Scheme 1a

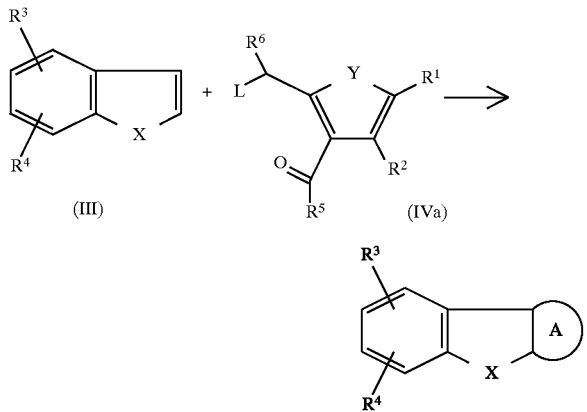

wherein A) is

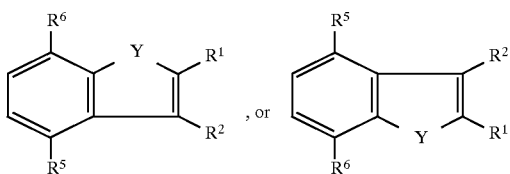

Intermediates of the type (IVa) may be prepared from compounds of the type (IV) (wherein R$^{11}$ is alkyl, eg ethyl) by reaction with the required amidoxime, as described above for 1,2,4-oxadiazoles and with hydrazine hydrate and a suitable ortho ester, as described above for 1,3,4-oxadiazoles.

Intermediates of formula IIa with R$^2$=H and Y=NH may be prepared by the reaction of compounds V and VI under basic conditions at a temperature between −20° C. and +20° C. The reaction proceeds via an azide intermediate (VIII) which is cyclised to IIa by heating in an appropriate solvent, e.g. xylene.

Scheme 2

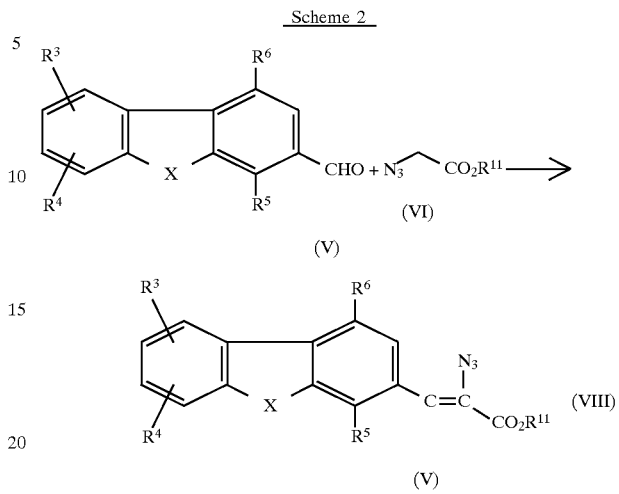

It is thereafter possible for the skilled man to synthesise compounds of the invention by the use and adaptation of known procedures (see Comprehensive Heterocyclic Chemistry, Supra).

For Example:

A: Carboxylic acids of the formula (II) may be converted to 2-substituted-1,3-oxazolines, 2-substituted-1,3-oxazines, 2-substituted-1,3-thiazolines or 2-substituted imidazolines by reaction with the appropriate 2-aminoethanol, 3-aminopropanol, 2-aminoethanethiol or 1,2-diaminoethane in the presence of triphenyl phosphine, a tertiary amine base (e.g. triethylamine or diisopropylethylamine) and carbon tetrachloride, with the solvent preferably being acetonitrile or a 1:1 mixture of acetonitrile-pyridine as described by H. Vorbruggen & K. Krolikiewicz, Tetrahedron Lett. 22, 4471–4474, 1981.

B: Alternatively, carboxylic acids of the formula (II) may be converted directly to the 2-substituted 1,3-oxazoline by reaction with a 2-aminoethanol in a suitable solvent at reflux (between 60° and 150° C.) as described in T. Green "Protecting Groups in Organic Synthesis", 1st Ed. Wiley Interscience, New York, 1981 p185.

C: Alternatively, carboxylic acids of the formula (II) or ethyl esters (compounds of the formula (IIa) wherein R$^{11}$ is ethyl) may be converted to the (2-hydroxyethyl)amides by usual methods followed by a cyclisation—dehydration reaction, e.g. using triphenylphosphine and diethylazodicarboxylate (P. Wipf and C. P. Miller, Tetrahedron Lett: 33 907–910, 1992), to give the 1,3-oxazoline.

D: Similarly, compounds of the formula (I) wherein R$^1$ is the 2-substituted-5-methyl oxazole may be produced from the corresponding propargylamide (prepared from the acid or amide by standard methods) by cyclisation using mercury (II) acetate in refluxing acetic acid (J. Sanders et al, J.Med.Chem. 1990, 33, 1128–1138).

E: Carboxylic acids of the formula (II) may be converted to the corresponding 2-oxoalkylamides by reaction with the 2-oxoalkylamine under standard conditions. These may then be converted to:

(i) 2-substituted thiazoles by reaction with Lawesson's Reagent in refluxing THF;

(ii) 1-methyl-2-substituted imidazoles by reaction with methylamine (as a THF solution) and acetic acid in refluxing xylene with azeotropic removal of water;

(iii) 2-substituted oxazoles by reaction with triphenylphosphine (3eq), DBU (3eq) and carbon tetrachloride in 1:1 pyridine acetonitrile at room temperature. (T. D. Gordon et al Tetrahedron Lett 34, 1901–4, 1993).

F:
(i) Compounds of the formula (I) wherein $R^1$ is the 3-methyl-5-substituted-pyrazole may be produced by conversion of the methyl ketone by reaction with the dimethyl acetal of N,N-dimethylacetamide followed by reaction with hydrazine hydrate in acetic acid.
(ii) The methyl ketone may also be converted to the 3-methyl-5-substituted-isoxazole by reaction with the dimethylacetal of N,N-dimethylacetamide followed by reaction with hydroxylamine in ethanol. (W. R. Tully et al, J.Med.Chem, 1991, 34, 2060–2067).

In fact methodology for preparing a range of compounds of the formula (I) from an ethyl ester, via the acid, the alcohol and the hydrazide is given in W. R. Tully, C. R. Gardner, R. J. Gillespie, R. Westwood, J.Med.Chem, 1991, 34, 2060–2067.

This gives methodology for, inter alia, the following options of $R^1$;
3-substituted-1,2,4-triazoles;
5-substituted-1,2,4-oxadiazoles;
3-substituted-1,2,4-oxadiazoles;
3-substituted-1,2-pyrazoles;
5-substituted-1,2-isoxazoles;
2-substituted-1,3,4-thiadiazoles;
2-substituted-1,3,4-oxadiazoles;
2-substituted-1,3-thiazoles; and
5-substituted-1,3-oxazoles;

In another aspect the invention relates to novel intermediates of the formulae (II), (III), (IV), (V) or (VII)

Compounds of the general formula (I) have been tested against two specially developed cell lines which are clones of the human fibrosarcoma cell-line, HT1080.

One clone, HT1080scc2, retains the transformed phenotype of the parental line, whilst the other, HT1080lc, is a morphologically flat, non-tumourigenic, revertant.

Thus, the effects of potential anti-tumour compounds can be evaluated on the basis of their ability to effect detransformation in HT1080scc2 cells.

Compounds of the present invention have been found to be particularly effective in this assay system.

In addition, compounds of the present invention have been found to be effective against DLD-1 colon carcinoma, SKOV-3 ovarian carcinoma and HB4A human breast tumour cell lines.

The compounds also exhibit low toxicity against normal cells.

Thus, the compounds of the present invention are useful for the treatment or prophylaxis of tumours. They may be employed in the treatment or prophylaxis of various forms of cancer of mammals including carcinomas, for instance of the stomach, pancreas, breast, uterus and colon; adenocarcinomas, for instance of the lung and colon; sarcomas, for instance fibrosarcoma; leukaemias, for instance lymphocytic leukaemia and lymphomas, for instance myeloid lymphoma.

The invention thus further provides a method for the treatment or prophylaxis of tumours in animals, including mammals, and especially humans, which comprises the administration of a clinically useful amount of compound of formula (I) or a pharmaceutically acceptable salt or physiologically functional derivative in a pharmaceutically useful form, once or several times a day or in any other appropriate schedule, orally, rectally, parenterally, or applied topically.

In addition, there is provided as a further, or alternative, aspect of the invention, a compound of formula (I) or a pharmaceutically acceptable salt or physiologically functional derivative thereof for use in therapy, for example as an antitumour agent.

The amount of a compound of formula (I) required to be effective against the aforementioned tumours will, of course, vary and is ultimately at the discretion of the medical or veterinary practitioner. The factors to be considered include the condition being treated, the route of administration, the nature of the formulation, the mammal's body weight, surface area, age and general condition, and the particular compound to be administered. A suitable effective antitumour dose is in the range of about 0.01 to about 100 mg/kg body weight, eg 0.1 to about 100 mg/kg body weight, preferably 1–30 mg/kg body weight. The total daily dose may be given as a single dose, multiple doses, e.g., two to six times per day or by intravenous infusion for selected duration. For example, for a 75 kg mammal, the dose range would be about 8 to 900 mg per day, and a typical dose could be about 50 mg per day. If discrete multiple doses are indicated treatment might typically be 15 mg of a compound of formula (I) given up to 4 times per day.

Whilst it is possible for the active compound to be administered alone, it is preferable to present the active compound in a pharmaceutical formulation. Formulations of the present invention, for medical use, comprise a compound of formula (I) or a salt or physiologically functional derivative thereof together with one or more pharmaceutically acceptable carriers and optionally other therapeutic ingredients. The carrier(s) should be pharmaceutically acceptable in the sense of being compatible with the other ingredients of the formulation and not deleterious to the recipient thereof.

The present invention, therefore, further provides a pharmaceutical formulation comprising a compound of formula (I) or a pharmaceutically acceptable salt or physiologically functional derivative thereof together with a pharmaceutically acceptable carrier thereof.

There is also provided a method for the preparation of a pharmaceutical formulation comprising bringing into association a compound of formula (I) or a pharmaceutically acceptable salt or physiologically functional derivative thereof, and a pharmaceutically acceptable carrier thereof.

Formulations according to the present invention include those suitable for oral, topical, rectal or parenteral (including subcutaneous, intramuscular and intravenous) administration. Preferred formulations are those suitable for oral or parenteral administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into desired formulations.

Formulations of the present invention suitable for oral administration may be presented as discrete units such as capsules, cachets, tablets or lozenges, each containing a predetermined amount of the active compound; as a powder or granules; or a solution or suspension in an aqueous or non-aqueous liquid such as a syrup, an elixir, an emulsion or a draught.

A tablet may be made by compression or moulding, optionally with one or more accessory ingredients. Compressed tablets may be prepared by compressing in a suitable machine the active compound in a free-flowing form such as a powder or granules, optionally mixed with a binder, lubricant, inert diluent, surface active or dispersing agent. Moulded tablets may be made by moulding in a suitable machine a mixture of the powdered active compound with any suitable carrier.

A syrup may be made by adding the active compound to a concentrated, aqueous solution of a sugar, for example sucrose, to which may also be added any accessory ingredients. Such accessory ingredients(s) may include flavourings, an agent to retard crystallisation of the sugar or an agent to increase the solubility of any other ingredients, such as a polyhydric alcohol for example glycerol or sorbitol.

Formulations for rectal administration may be presented as a suppository with a conventional carrier such as cocoa butter.

Formulations suitable for parenteral administration conveniently comprise a sterile aqueous preparation of the active compound which is preferably isotonic with the blood of the recipient. Such formulations suitably comprise a solution of a pharmaceutically and pharmacologically acceptable acid addition salt of a compound of the formula (I) that is isotonic with the blood of the recipient.

Useful formulations also comprise concentrated solutions or solids containing the compound of formula (I) which upon dilution with an appropriate solvent give a solution for parenteral administration as above.

In addition to the aforementioned ingredients, the formulations of this invention may further include one or more accessory ingredient(s) selected from diluents, buffers, flavouring agents, binders, surface active agents, thickeners, lubricants, preservatives (including antioxidants) and the like.

In a further aspect the present invention provides the use of a compound of formula (I) or a pharmaceutically acceptable salt or physiologically functional derivative thereof for the manufacture of a medicament for the treatment of tumours.

The invention will now be illustrated by the following non-limiting Examples in which:

All temperatures are in degrees Celcius (° C.) IR spectra were recorded on a Perkin-Elmer 257 grating spectrophotometer or a Bruker FS66 spectrophotometer.

U.V. spectra were measured in ethanol on a Unicam SP800 spectrophotometer. 1H NMR spectra were obtained on a Bruker WM 360-NMR spectrophotometer at 360 MHz, or on a Bruker AC200 spectrophotometer at 200 MHz. J values are given in Hz.

Mass spectra were obtained on Varian CH5D(EI), Kratos Concept (EI) or Kratos Ms50(FAB) instruments.

Ethyl 4-methyl-1H-[1]benzothieno[2,3-$f$]indole-2-carboxylate

Sodium (1.6 g, 70 mmol) was dissolved in dry ethanol (175 ml) and the solution cooled to 0° C. A mixture of 4-methyldibenzothiophene-3-carboxaldehyde (prepared according to the method of E. Campaigne et al., J. Heterocyclic Chem., 6, 553 (1969)) (4.0 g, 18 mmol) and ethyl 2-azidoacetate (11.7 g, 91 mmol) in THF (25 ml) was added dropwise to the sodium ethoxide solution. The reaction mixture was stirred at 0° C. for 3 h giving a yellow precipitate. This was collected by filtration and dissolved in ether, and the resulting solution was filtered and concentrated in vacuo to give an unstable yellow solid (2.86 g). This solid was added to xylene (150 ml) at reflux, and heating continued for 5 min. The reaction mixture was cooled and concentrated in vacuo. The material was triturated with ethyl acetate/petrol to give the product as a yellow solid (1.38 g, 25% from the aldehyde) with m.p. 219°–220° C. (Found: C, 69.63; H, 4.81; N, 4.31. $C_{18}H_{15}NO_2S$ requires: C, 69.88; H, 4.89; N, 4.53%); δH [$^2H_6$]-DMSO 12.08 (1H, s, 1-NH), 8.25–8.38 (1H, m, 9-H), 8.19 (1H, s, 10-H), 7.89–8.00 (1H, m, 6-H), 7.42–7.58 (2H, m, 7-H, 8-H), 7.48 (1H, s, 3-H), 4.39 (2H, q, J 6.5, OC$\underline{H}_2$CH$_3$), 2.74 (3H, s, 4-CH$_3$), 1.43 (3H, t, J 7, OCH$_2$C$\underline{H}_3$); m/z (%) 309 (78, M$^+$), 263 (100), 235 (35); $\nu_{max}$ (KBr disc)/cm$^{-1}$ 3325, 1686, 1215.

4-Methyl-1H-[1]benzothieno[2,3-$f$]indole-2-carboxylic acid

Ethyl 4-methyl-1H-[1]benzothieno[2,3-$f$]indole-2-carboxylate (1.0 g, 3.2 mmol) was suspended in a mixture of methanol (110 ml) and water (30 ml). Caesium carbonate (10 g) was added and the mixture was heated at reflux under nitrogen for 2 h. The solution was allowed to cool to room temperature, and the methanol was removed in vacuo. The solution was acidified with 0.1 Molar hydrochloric acid and the resulting yellow precipitate was collected by fitration and washed with water. The wet precipitate was dissolved in acetone and the solvent removed in vacuo to give the product as a yellow solid with m.p. 271°–272° C.; δH [$^2H_6$]-DMSO 11.88 (1H, s, 1-NH), 8.29 (1H, dd, J 6, 3, 9-H), 8.18 (1H, s, 10-H), 7.89–7.99 (1H, m, 6-H), 7.44–7.54 (2H, m, 7-H, 8-H), 7.35 (1H, d, J 2, 3-H), 2.72 (3H, s, 4-CH$_3$); m/z (%) 281 (90, M$^+$), 263 (100), 235 (69).

EXAMPLE 1 a): Ethyl 3,4-dimethyl pyrrolo[2,3-b]carbazole-2-carboxylate

This compound was prepared as a by-product in the reaction of indole with ethyl 5-acetoxymethyl4-acetyl-3-methylpyrrole-2-carboxylate in toluene in the presence of K-10 Montmorillonite Clay to form ethyl 3,4-dimethyl pyrrolo[3,2-b]carbazole-2-carboxylate. For example, reaction of indole (13.16 g, 112.36 mmol) with the pyrrole (15.0 g, 56.18 mmol) and clay (45 g) in toluene (700 ml) at reflux gave the [3,2-b]-isomer as the major product (8.20 g, 48%) (as previously reported in WO 93/01512) and the [2,3-b]-isomer as the minor product (0.69 g, 4%) as a pale green solid which decomposes above 200° C. δH [$^2H_6$]-DMSO 11.05 and 10.88 (2×1H, 2×s, 1-NH, 9-NH), 8.18 (1H, d, J 7.5, 5-H), 7.27–7.43 (2H, m, 7H, 8H), 7.21 (1H, s, 10-H), 7.11 (1H, ddd, J 7.5, 5.5, 2, 6-H), 4.37 (2H, q, 7.5, C$\underline{H}_2$CH$_3$), 3.20 and 2.98 (2×3H, 2×s, 3-CH$_3$ and 4-CH$_3$), 1.40 (3H, t, 7.5, CH$_2$C$\underline{H}_3$).

b): 3,4-Dimethyl pyrrolo[2,3-b]carbazole-2-carboxylic acid

Ethyl 3,4-dimethyl pyrrolo[2,3-b]carbazole-2-carboxylate (0.589 g, 1.93 mmol) was dissolved in methanol (250 ml) and treated with 2N aqueous sodium hydroxide solution (24 ml, 48 mmol). The mixture was heated to reflux for 24 hours, by which time TLC showed complete conversion of ester to acid. The reaction mixture was filtered and concentrated in vacuo to a volume of ca.40 ml. This was acidified to pH 3, left to stand for 1 hour at 4° C., and then filtered to give the acid as a bright yellow precipitate which decomposes above 170° C. δH [$^2H_6$]-DMSO 10.95 and 10.86 (2×1H, 2×s, 1-NH, 9-NH), 8.19 (1H, d, J 7.5, 5-H), 7.25–7.43 (2H, m, 7-H, 8-H), 7.19 (1H, s, 10-H), 7.13 (1H, ddd, J 8, 6, 2, 6-H), 3.19 and 2.95 (2×3H, 2×s, 3-CH$_3$ and 4-CH$_3$).

EXAMPLE 2

3,4-Dimethyl-2-(3-ethyl-1,2,4-oxadiazol-5-yl) pyrrolo[3,2-b]carbazole 3,4-Dimethylpyrrolo[3,2-b]carbazole-2-carboxylic acid (2.78 g, 10.0 mmol), (prepared as described in WO93/01512) and carbonyl diimidazole (1.85 g, 11.4 mmol) were dissolved in freshly distilled tetrahydrofuran (50 ml) in an oven-dried flask under a nitrogen atmosphere. The resulting orange solution was stirred at room temperature for three hours, by which time it was an orange suspension, and complete conversion of the acid to the imidazolide intermediate was verified by TLC. Meanwhile, in a second oven-dried flask, ethylamidoxime (2.2 g, 25 mmol) was dissolved in THF (50 ml). To this was added crushed 3 Å sieves (3.3 g) and the mixture was stirred at room temp for 45 min. Sodium hydride (60% dispersion in mineral oil, 0.804 g, 20 mmol) was added and the mixture stirred for a further 2.5 hours. The contents of the two flasks were combined and stirred at room temp for 18 hours, by which time TLC showed complete consumption of the imidazolide intermediate. The solvent was removed in vacuo to give a yellow solid. Chromatography on silica (eluting with ethyl acetate/petrol, gradient 8% –15% ethyl acetate) gave a yellow solid. The majority of this material was dissolved in ether, leaving an insoluble orange impurity. The solution was filtered, and the solvent removed in vacuo to give the title compound as a yellow powder (1.2 g, 36%) which decomposes above 45° C. $\delta$H [$^2$H$_6$]-DMSO 11.69 (1H, s, 1-NH), 10.69 (1H, s, 5-NH), 8.09 (1H, d, J 7.5, 9-H), 7.90 (1H, s, 10-H), 7.30–7.48 (2H, m, 6-H, 7-H), 7.09 (1H ddd, J 7.5, 5.5, 2, 8-H), 2.99 and 2.95 (2×3H, 2×s, 3-CH$_3$ and 4-CH$_3$), 2.85 (2H, q, 7.5, C$\underline{H}_2$CH$_3$), 1.36 (3H, t, 7.5, CH$_2$C$\underline{H}_3$).

EXAMPLE 3

2-(3-Benzyl-1,2,4-oxadiazol-5-yl)-3,4-dimethylpyrrolo[3,2-b]carbazole 3,4-Dimethylpyrrolo[3,2-b]carbazole-2-carboxylic acid (0.278 g, 1.0 mmol) and carbonyl diimidazole (0.185 g, 1.1 mmol) were dissolved in freshly distilled tetrahydrofuran (5 ml) in an oven-dried flask under a nitrogen atmosphere. The resulting orange solution was stirred at room temperature for two hours, by which time it was an orange suspension, and complete conversion of the acid to the imidazolide intermediate was verified by TLC. Meanwhile, in a second oven-dried flask benzylamidoxime (0.30 g, 2.0 mmol) was dissolved in THF (5 ml). To this was added crushed 3 Å sieves (0.33 g) and the mixture was stirred at room temp for 1 hour. Sodium hydride (60% dispersion in mineral oil, 0.80 g, 2.0 mmol) was added and the mixture stirred for 1 hour further. The contents of the two flasks were combined and heated at reflux for 2 hours, by which time TLC showed complete consumption of the imidazolide intermediate. The solvent was removed in vacuo to give a yellow solid. Chromatography on silica (eluting with ethyl acetate/petrol, gradient 8% –16% ethyl acetate) gave the oxadiazole product (0.10 g 26%). Recrystallisation of a portion from ethyl acetate/petrol gave a yellow powder with m.p. 281°–283° C. (decomp.). $\delta$H [$^2$H$_6$]-DMSO 11.69 (1H, s, 1-NH), 10.67 (1H, s, 5-NH), 8.10 (1H, d, J 7.5, 9-H), 7.89 (1H, s, 10-H), 7.24–7.48 (7H, m, 6-H, 7-H, PhH), 7.09 (1E, ddd, J 7.5, 5.5, 2, 8-H), 4.22 (2H, s, PhCH$_2$), 2.98 and 2.93 (2×3H, 2×s, 3-CH$_3$ and 4-CH$_3$).

EXAMPLE 4

3,4-Dimethyl-2-(3-ethyl-1,2,4-oxadiazol-5-yl) pyrrolo[2,3-b]carbazole 3,4-Dimethylpyrrolo[2,3-b]carbazole-2-carboxylic acid (0.49 g, 1.76 mmol) and carbonyl diimidazole (0.33 g, 1.94 mmol) were dissolved in freshly distilled tetrahydrofuran (10 ml) in an oven-dried flask under a nitrogen atmosphere and this solution was stirred at room temperature for three hours. Meanwhile, in a second oven-dried flask, ethylamidoxime (0.39 g 4.43 mmol) was dissolved in THF (5 ml). To this was added crushed 3 Å sieves and the mixture was stirred at room temp for 45 min. Sodium hydride (60% dispersion in mineral oil, 0.142 g, 3.5 mmol) was added and the mixture stirred for a further 2.5 hours. The contents of the two flasks were combined (with further 10 ml THF) and stirred at room temp for 18 hours, by which time TLC showed complete consumption of the imidazolide intermediate. The solvent was removed in vacuo to give a yellow solid. Chromatography on silica (eluting with 25% ethyl acetate/hexane) gave the title compound as a yellow solid (0.150 g, 26%) with m.p. 258°–260° C. (decomp.). (Found: C, 72.03; H, 5.28; N, 16.42. C$_{20}$H$_{18}$N$_4$O 0.08EtOAC requires: C, 72.33; H, 5.57; N, 16.60%); $\delta$H [$^2$H$_6$]-DMSO 11.55 (1H, s, 1-NH), 10.94 (1H, s, 9NH), 8.19 (1H, d, J 7.5, 5-H), 7.29–7.43 (2H, m, 7-H, 8-H), 7.22 (1H, s, 10-H), 7.13 (1H, ddd, J 8, 5.5, 2, 6-H), 3.20 and 3.03 (2×3H, 2×s, 3—CH$_3$ and 4—CH$_3$), 2.83 (2H, q, 7.5, C$\underline{H}_2$CH$_3$), 1.37 (3H, t, 7.5, CH$_2$C$\underline{H}_3$); m/z (%) 330 (100, M$^{+)}$, 260 (34), 232 (29); $\nu_{max}$ (KBr disk)/cm$^{-1}$ 3394, 1599, 1259.

EXAMPLE 5

2-(3-Ethyl-1,2,4-oxadiazol-5-yl)-4-methyl-1H-[1] benzothieno[2,3-ƒ]indole

4-Methyl-1H-[1]benzothieno[2,3-ƒ]indole 2-carboxylic acid (0.281 g, 1.0 mmol) and carbonyl diimidazole (0.185 g, 1.1 mmol) were dissolved in freshly distilled tetrahydrofuran (5 ml) in an oven-dried flask under a nitrogen atmosphere for two hours. Meanwhile, in a second oven-dried flask ethylamidoxime (0.24 g, 2.7 mmol) was dissolved in THF (5 ml). To this was added crushed 3 Å sieves (0.33 g) and the mixture was stirred at room temp for 1 hour. Sodium hydride (60% dispersion in mineral oil, 0.081 g, 2.0 mmol) was added and the mixture stirred for 1 hour further. The contents of the two flasks were combined and stirred at room temp for 24 hours, by which time TLC showed complete consumption of the imidazolide intermediate. The solvent was removed in vacuo to give a yellow solid, which was dissolved in ethyl acetate and filtered through a plug of silica. The solvent was again removed in vacuo and the residue obtained was dissolved as far as possible in ether and filtered. The filtrate was concentrated in vacuo and the resulting solid was purified by chromatography on silica (eluting with toluene) to give the title compound as a yellow solid (0.035 g, 10%) with m.p. 231°–233° C. (decomp.). $\delta$H [$^2$H$_6$]-DMSO 12.57 (1H, s, 1-NH), 8.30–8.39 (1H, m, 9-H), 8.2 (1H, s, 10-H), 7.93–8.00 (1H, m, 6-H), 7.61 (2H, s, 3-H), 7.47–7.55 (2H, m, 7-H, 8-H), 2.85 (2H, q, 7.5, CH$_2$CH$_3$), 2.76 (3H, s, 4-CH$_3$), 1.34 (3H, t, 7.5, CH$_2$CH$_3$).

EXAMPLE 6

3,4-Dimethyl-2-(2-methyl-1,3 4-oxadiazol-5-yl)-pyrrolo[3,2-b]carbazole 3,4-Dimethyl-2-(hydrazinocarbonyl) pyrrolo[3,2-b] carbazole (prepared as described in WO93/01512) (0.430 g, 1.47 mmol) was dissolved in dry benzene (24 ml). To this was added triethyl orthoacetate (8.41 g, 51.9 mmol) and the resulting suspension was heated at reflux for 27 hours, by which time TLC showed no remaining hydrazide. The solvent and excess triethyl orthoacetate were removed in vacuo to give a yellow solid. This was suspended in ethyl acetate and washed with water. The undissolved solid was collected by filtration of the organic phase and dried to give the oxadiazole product (0.10 g, 22%). Recrystallisation of a portion from dimethylformamide/water gave a yellow powder which decomposes above 100° C. δH [$^2$H$_6$]-DMSO 11.51 (1H, s, 1-NH), 10.65 (1H, s, 5-NH), 8.09 (1H, d, J 7.5, 9-H), 7.90 (1H, s, 10-H), 7.30–7.48 (2H, m, 6-H, 7-H), 7.02–7.12 (1H, m, 8-H), 2.94 (6H, s, 3-CH$_3$ and 4-CH$_3$), 2.63 (3H, s, 2'-CH$_3$).

EXAMPLE 7

3,4-Dimethyl-2-(2-ethyl-1,3,4-oxadiazol-5-yl)-pyrrolo[3,2-b]carbazole 3,4-Dimethyl-2-(hydrazinocarbonyl)pyrrolo[3,2-b] carbazole (0.52 g, 1.78 mmol) was dissolved in dry benzene (29 ml). To this was added triethyl orthopropionate (10.39 g, 58.95 mmol) and the resulting suspension was heated at reflux for 30 hours, by which time TLC showed no remaining hydrazide. The solvent and excess triethyl orthopropionate were removed in vacuo to give a yellow solid. This was recrystallised from dimethylformamide/water to give the oxadiazole product as a yellow solid (0.27 g, 40%) with m.p. 235°–236° C. (decomp.). δH [$^2$H6]-DMSO 11.50 (1H, s, 1-NH), 10.63 (1H, s, 5-NH), 8.09 (1H, d, J 7.5, 9-H), 7.97 (0.5H, s, 1-H of DMF), 7.89 (1H, s, 10-H), 7.30–7.48 (2H, m, 6-H, 7-H), 7.09 (1H, ddd, J 7.5, 5.5, 1.5, 8-H), 2.99 (2H, q, J 7.5, C$\underline{H}_2$CH$_3$), 2.94 (6H, s, 3-CH$_3$ and 4-CH$_3$), 2.90 and 2.75 (2×1.5H, 2×s, NMe$_2$ of DMF), 1.39 (3H, t, J 7.5, CH$_2$C$\underline{H}_3$).

EXAMPLE 8

3,4-Dimethyl-2-(2-phenyl-1,3,4-oxadiazol-5-yl)-pyrrolo[3,2-b]carbazole 3,4-Dimethyl-2-(hydrazinocarbonyl)pyrrolo[3,2-b] carbazole (0.41 g, 1.4 mmol) was dissolved in dry xylene (25 ml). To this was a dded triethyl orthobenzoate (11.12 g, 45.6 mmol) and the resulting suspension was heated at reflux for 9 days, by which time TLC showed no remaining hydrazide. The reaction mixture was allowed to cool, and the resulting suspension filtered to give a yellow solid (0.305 g, 57%). A portion was recrystallised from dimethylformamide/water to give the oxadiazole product as orange crystals with m.p. 280° C. (decomp.). δH [$^2$H$_6$]-DMSO 11.65 (1H, s, 1-NH), 10.69 (1H, s, 5-NH), 8.09–8.23 (3H, m, 9-H, 2'-H, 6'-H), 7.92–7.99 (2H, m 10-H, 1-H of DMF),), 7.65–7.75 (3H, m, 3'-H, 4'-H, 5'H), 7.31–7.49 (2H, m, 6-H, 7-H), 7.10 (1H, ddd, J 7.5, 6, 1.5, 8-H), 3.03 and 2.98 (2×3H, s, 3-CH$_3$ and 4-CH$_3$), 2.90 and 2.74 (2×3H, 2×s, NMe$_2$ of DMF).

EXAMPLE 9

2-(2-Ethyl-1,3,4-oxadiazol-5-yl)-4-methyl-1H-[1]benzothieno[2,3-ƒ]indole

Ethyl 4-methyl-1H-[1]benzothieno[2,3-ƒ]indole 2-carboxylate (0.60 g, 1.94 mmol) was mixed with hydrazine hydrate (6 ml) and heated in a sealed flask at 120° C. for 6 hours. The reaction was allowed to cool to room temperature, shaken vigourously and heated at 120° C. again for 2 hours. The reaction was allowed to cool and the solid collected by filtration, washed with water and dried in vacuo at 25° C. This gave the hydrazide as a pale yellow solid (0.50 g, 87%), which was not further characterised. The hydrazide (0.50 g, 1.70 mmol) was dissolved in dry toluene (25 ml)

together with triethyl orthopropionate (10 ml) and the resulting mixture was heated at reflux under a nitrogen atmosphere for 7 hours. The reaction was allowed to cool, and the precipitate was collected by fitration and washed with toluene and petrol. Recrystallisation from toluene gave an off-white solid (0.345 g, 53% from the ethyl ester) with m.p. 319°–321° C. (decomp.). δH [$^2$H$_6$]-DMSO 8.13–8.30 (2H, m, 9H, 10-H), 7.82–7.96 (1H, m, 6-H), 7.39–7.50 (2H, m, 7-H, 8-H) 7.29–7.38 (1H, m, 3-H), 3.00 (2H, q, J 7, C$\underline{H}_2$CH$_3$), 2.73 (3H, s, 4-CH$_3$), 1.39 (3H, t, J 7.5, CH$_2$C$\underline{H}_3$).

EXAMPLE 10

3,4-Dimethyl-2-[3-(3,4-methylenedioxyphenyl)-1,2,4-oxadiazol-5-yl]pyrrolo[3,2-b]carbazole 3,4-Dimethylpyrrolo[3,2-b]carbazole-2-carboxylic acid (0.3 g, 1.8 mmol), (prepared as described in WO93/01512) and carbonyl diimidazole (0.366 g, 1.98 mmol) were dissolved in freshly distilled tetrahydrofuran (9 ml) in an oven-dried flask under a nitrogen atmosphere. The resulting orange solution was stirred at room temperature for three hours, by which time it was an orange suspension, and complete conversion of the acid to the imidazolide intermediate was verified by TLC. Meanwhile, in a second oven-dried flask, 3,4-methylenedioxyphenyl (0.486 g, 2.7 mmol) was dissolved in THF (9 ml). To this was added crushed 3 Å sieves (0.59 g) and the mixture was stirred at room temp for 30 min. Sodium hydride (60% dispersion in mineral oil, 0.144 g, 3.6 mmol) was added and the mixture stirred for a further 45 min. The contents of the two flasks were combined and stirred at room temp for 18 hours, by which time TLC showed complete consumption of the imidazolide intermediate. The solvent was removed in vacuo to give a yellow solid. Chromatography on silica (eluting with ethyl acetate/petrol, gradient 10%–35% ethyl acetate) gave a yellow solid. This material was triturated with hot methanol to leave the pure product (0.045 g, 13%) with m.p. 260° C. (decomp.) (Found: C, 70.87; H, 4.24; N, 12.98. C$_{25}$H$_{18}$N$_4$O$_3$ requires: C, 71.08; H, 4.30; N, 13.26%); δH [$^2$H$_6$]-DMSO 11.75 (1H, s, 1-NH), 10.65 (1H, s, 5-NH), 8.11 (1H, d, J 7.5, 9-H), 7.93 (1H, s, 10-H), 7.72 (1H, dd, J 7.8, 2, 6'-H), 7.56 (1H, d, J 2, 2'-H), 7.48–7.32 (2H, m, 6-H, 7-H), 7.15 (1H, d, J 7.8, 5'-H), 7.12–7.04 (1H, m, 8-H), 6.17 (2H, s, OCH$_2$O) 3.05 and 2.95 (2×3H, 2×s, 3-CH$_3$ and 4-CH$_3$); m/z (%) 422 (15, M$^+$), 259 (72), 232 (19); ν$_{max}$ (KBr disc)/cm$^{-1}$ 3437, 1603, 1574, 1535.

EXAMPLE 11

4-Methyl-2-(2-oxazolin-2-yl)-1H-[1]benzothieno[2,3-ƒ]indole

N-(2-Hydroxyethyl)4-methyl-1H-[1]benzothieno[2,3-ƒ]indole-2-carboxamide

Ethyl 4-methyl-1H-[1]benzothieno[2,3ƒ]indole-2-carboxylate (500 mg, 1.62 mmol) was mixed with ethanolamine (2 ml) and heated at reflux under nitrogen for one hour. The excess ethanolamine was removed in vacuo and the residue was triturated with ethyl acetate. The resulting solid was recrystallised from DMF/water to give the product (0.390 g, 74%) with m.p. 230°–230° C. (Found: C, 65.64; H, 4.90 N, 8.61. C$_{18}$H$_{16}$N$_2$O$_2$S.0.25H$_2$O requires: C, 65.73; H, 5.06; N, 8.52%); δH [$^2$H$_6$]-DMSO 11.78 (1H, s, 1-NH), 8.55 (1H t, J 5.5, amide N-H), 8.21–8.31 (1H, m, 9-H), 8.17 (1H, s, 10-H), 7.89–7.99 (1H, m, 6-H), 7.42–7.25 (2H, m, 7-H, 8-H), 7.34 (1H, s, 3-H), 4.79 (1H, t, J 5.5, O-H), 3.59 (2H, quartet, J 6, 2'-H$_2$), 3.42 (2H, quartet, J 6, 1'-H$_2$), 2.71 (3H, s, 4-CH$_3$); m/z (%) 325 (100, M+1$^+$), 264 (63); $v_{max}$ (KBr disc)/cm$^{-1}$ 3396, 1616, 1574, 1564, 1304.

N-(2-Chloroethyl)-4-methyl-1H-[1]benzothieno2,3-ƒ]indole-2-carboxamide

N-(2-Hydroxyethyl)4-methyl-1H-[1]benzothieno[2,3-ƒ]indole-2-carboxamide (0.100 g, 0.31 mmol) was mixed with triphenylphosphine (0.160 g, 0.61 mmol) and carbon tetrachloride (8 ml) in DMF (1 ml). The mixture was heated to reflux for six hours and then allowed to cool to room temperature. The solvents were removed in vacuo to give an oil. Chromatography (eluting with 75% ethyl acetate/petrol) gave a brown solid. This was redissolved in ethyl acetate, the solution filtered and the solvent removed in vacuo to give the product as a yellow solid (0.073 g, 69%); δH [$^2$H$_6$]-DMSO 11.81 (1H, s, 1-NH), 8.82 (1H, t, J 5.5, amide N-H), 8.20–8.31 (1H, m, 9-H), 8.15 (1H, s, 10-H), 7.89–7.98 (1H, m, 6-H), 7.42–7.51 (2H, m, 7-H, 8-H), 7.34 (1H, s, 3-H), 3.79 (2H, t, J 5.5, 2'-H$_2$), 3.65 (2H, quartet, J 5, 1'-H$_2$), 2.70 (3H, s, 4-CH$_3$); m/z (%) 342 (26, M$^+$), 306 (100), 263 (92), 235 (82); $v_{max}$ (KBr disc)/cm$^{-1}$ 3290, 1657, 1539.

N-(2-Chloroethyl)-4-methyl-1H-[1]benzothieno[2,3-ƒ]indole-2-carboxamide (0.034 g, 0.1 mmol) was suspended in absolute ethanol (2 ml) and heated to reflux. A solution of sodium hydroxide (0.008 g, 0.2 mmol) in 75% ethanol (0.2 ml) was added and the reaction was heated to reflux for 1 minute. The reaction was diluted with water and the title compound was filtered off as a yellow solid (0.018 g, 60%) with m.p. 195°–197° C. (Found: C, 69.25; H, 4.47; N, 8.86. C$_{18}$H$_{14}$N$_2$OS.0.3H$_2$O requires: C, 69.34; H, 4.72; N, 8.99%); δH [$^2$H$_6$]-DMSO 11.9 (1H, b, NH), 8.25 (1H, m), 8.15 (1H, s), 7.95 (1H, m), 7.45 (2H, m), 7.1 (1H, s), 4.45 (2H, t), 4.05 (2H, t), 2.7 (3H, s, CH$_3$); m/z 306 (M$^+$); $v_{max}$ (KBr disc)/cm$^{-1}$ 3203, 3172, 1659.

EXAMPLE 12

3,4-Dimethyl-2-(3-methyl-1,2,4-oxadiazol-5-yl)pyrrolo[3,2-b]carbazole 3,4-Dimethylpyrrolo[3,2-b]carbazole-2-carboxylic acid (0.556 g, 2 mmol), (prepared as described in WO93/01512) and carbonyl diimidazole (0.37 g, 2.2 mmol) were dissolved in freshly distilled tetrahydrofuran (10 ml) in an oven-dried flask under a nitrogen atmosphere. The resulting orange solution was stirred at room temperature for two hours, by which time it was an orange suspension, and complete conversion of the acid to the imidazolide intermediate was verified by TLC. Meanwhile, in a second oven-dried flask, methylamidoxime (0.326 g, 4.4 mmol) was dissolved in THF (20 ml). To this was added crushed 3 Å sieves (0.59 g) and the mixture was stirred at room temp for 1 hour. Sodium hydride (60% dispersion in mineral oil, 0.161 g, 4 mmol) was added and the mixture stirred for a further 1 hour. The contents of the two flasks were combined and stirred at room temp for 18 hours, by which time TLC showed complete consumption of the imidazolide intermediate. The solvent was removed in vacuo to give a yellow solid. Chromatography on silica (eluting with ethyl acetate/petrol, gradient 10%–25% ethyl acetate) gave a yellow solid. This material was crystallised from DMF/water and dried (high vacuum/100° C.) to give the pure yellow product (0.18 g, 28%) with m.p. 270° C. (decomp.) (Found: C, 72.11; H, 5.02; N, 17.39. C$_{19}$H$_{16}$N$_4$O requires: C, 72.13; H, 5.10; N, 17.71%); δH [$^2$H$_6$]-DMSO 11.69 (1H, s, 1-NH), 10.65 (1H, s, 5-NH), 8.10 (1H, d, J 7.5, 9-H), 7.90 (1H, s, 10-H), 7.45–7.32 (2H, m, 6-H, 7-H), 7.09 (1H, ddd, J 7.5, 5.5, 2, 8-H), 3.00 and 2.93 (2×3H, 2×s, 3-CH$_3$ and 4-CH$_3$), 2.45 (3H, s, 3'-CH$_3$); m/z (%) 316 (100, M$^+$), 272 (12), 260 (20), 247 (14), 231 (29); $v_{max}$ (KBr disc)/cm$^{-1}$ 3396, 1595, 1329, 1239.

EXAMPLE 13

3,4-Dimethyl-2-(3-methyl-1,2,4-oxadiazol-5-yl)pyrrolo[2,3-b]carbazole 3,4-Dimethylpyrrolo[2,3-b]carbazole-2-carboxylic acid (0.5 g, 1.8 mmol) and carbonyl diimidazole (0.34 g, 2 mmol) were dissolved in freshly distilled tetrahydrofuran (20 ml) in an oven-dried flask under a nitrogen atmosphere. The resulting orange solution was stirred at room temperature for two hours, by which time it was an orange suspension, and complete conversion of the acid to the imidazolide intermediate was verified by TLC. Meanwhile, in a second oven-dried flask, methylamidoxime (0.27 g, 3.6 mmol) was dissolved in THF (10 ml). To this was added crushed 3 Å sieves and the mixture was stirred at room temp for 45 mins. Sodium hydride (60% dispersion in mineral oil, 0.243 g, 6.12 mmol) was added and the mixture stirred for a further 2 hours. The contents of the two flasks were combined and stirred at room temp for 18 hours, by which time TLC showed complete consumption of the imidazolide intermediate. The solvent was removed in vacuo to give a yellow solid. Chromatography on silica (eluting with ethyl acetate/hexane 1:2) gave the pure yellow product (0.044 g, 8%) with m.p. 248°–249° C. (Found: C, 71.97; H, 5.07; N, 17.21. C$_{19}$H$_{16}$N$_4$O.0.05EtOAc requires: C, 71.89; H. 5.15; N, 17.47%); δH [$^2$H$_6$]-DMSO 11.54 (1H s, 1-NH), 10.92 (1H, s, 9-NH), 8.17 (1H, d, J 7.5, 5-H), 7.41–7.28 (2H, m, 7-H, 8-H), 7.19 (1H, s, 10-H), 7.16–7.06 (1H, m, 6-H), 3.18 and 3.00 (2×3H, 2×s, 3-CH$_3$ and 4-CH$_3$), 2.43 (3H, s, 3'-CH$_3$); m/z (%) 316 (100, M$^+$), 260 (19), 232 (31).

EXAMPLE 14

3,4-Dimethyl-2-[(3-phenyl)-1,2,4-oxadiazol-5-yl]pyrrolo[3,2-b]carbazole 3,4-Dimethylpyrrolo[3,2-b]carbazole-2-carboxylic acid (0.278 g, 1.0 mmol), (prepared as described in WO93/01512) and carbonyl diimidazole (0.185 g, 1.1 mmol) were dissolved in freshly distilled tetrahydrofuran (5 ml) in an oven-dried flask under a nitrogen atmosphere. The resulting orange solution was stirred at room temperature for 2.5 hours, by which time it was an orange suspension, and complete conversion of the acid to the imidazolide intermediate was verified by TLC. Meanwhile, in a second oven-dried flask, benzamidoxime (0.3 g, 2 mmol) was dissolved in THE (5 ml). To this was added crushed 3 Å sieves (0.333 g) and the mixture was stirred at room temp for 45 min. Sodium hydride (60% dispersion in mineral oil, 0.08 g, 2 mmol) was added and the mixture stirred for a further 1.75 hours. The contents of the two flasks were combined and stirred at room temp for 18 hours, by which time TLC showed complete consumption of the imidazolide intermediate. The solvent was removed in vacuo to give a red solid. Crystallisation from DMF/water gave a yellow solid (0.2 g, 53%). A small sample was recrystallised from DMF/water to yield pure, yellow product of m.p. >240° C. (decomp.). (Found: C, 74.56; H, 4.65; N, 14.46. C$_{24}$H$_{18}$N$_4$O 0.0.4H$_2$O requires: C, 74.75; H, 4.91; N, 14.53%); δH [$^2$H$_6$]-DMSO 11.78 (1H, s, 1-NH), 10.69 (1H, s, 5-NH), 8.20–8.06 (3H, m, 9-H and 2 of 3'-Ph), 7.95 (1H, s, 10-H), 7.70–7.61 (3H, m, 3 of 3'-Ph), 7.48–7.33 (2H, m, 6-H, 7-H), 7.10 (1H, ddd, J 7.5, 5.5, 2, 8-H), 3.09 and 2.95 (2×3H, 2×s, 3-CH$_3$ and 4-CH$_3$); m/z (%) 378 (100, M$^+$), 260 (62), 232 (34); $v_{max}$ (KBr disc)/cm$^{-1}$ 3437, 1601, 1498, 1444, 1365, 1344, 1308, 1240.

EXAMPLE 15

3,4-Dimethyl-2-(2-oxazolin-2-yl)pyrrolo[3,2-b] carbazole

N-(2-Hydroxyethyl)3,4-dimethylpyrrolo[3,2-b] carbazole-2-carboxamide

Ethyl 3,4-dimethylpyrrolo[3,2-b]carbazole-2-carboxylate (1.00 g, 3.26 mmol) was suspended in ethanolamine (5 ml) and heated at reflux (giving an orange solution) under nitrogen for 1.5 hours, by which time TLC showed no remaining starting material. The excess ethanolamine was removed in vacuo and the yellow residue was triturated with DCM. The resulting solid was recrystallised from ethanol/water to give the product (two crops combined) (0.383 g, 36.5%) with m.p. 270° C. (decomp.). δH [$^2$H$_6$]-DMSO 10.90 (1H, br s, 1-NH), 10.59 (1H, s, 5-NH), 8.09 (1H, d, J 9, 9-H), 7.89 (1H, t, J 5, amide NH), 7.85 (1H, s, 10-H), 7.29–7.45 (2H, m, 6-H, 7-H), 7.08 (1H, t, J 7.5, 8-H), 4.80 (1H, t, J 5,O-H) 3.60 (2H, quartet, J 6, 2'-CH$_2$), 3.23–3.50 (2H, m, 1'-CH$_2$), 2.92 and 2.86 (2×3H, 2×s, 3-CH$_3$ and 4-CH$_3$); m/z (%) 321 (87, M$^+$), 303 (72), 260 (100), 231 (64), 69 (67); $v_{max}$ (KBr disc)/cm$^{-1}$ 3334, 1587, 1543, 1309, 1250.

N-(2-Chloroethyl) 3,4-dimethylpyrrolo[3,2-b] carbazole-2-carboxamide

2-Hydroxyethyl 3,4-dimethylpyrrolo[3,2-b]carbazole-2-carboxamide (0.70 g, 2.18 mmol) was suspended in carbon tetrachloride (70 ml) under a nitrogen atmosphere and heated to reflux using a Dean-Stark apparatus to remove any water. The Dean-Stark was removed and dry DMF (14 ml) added to give a yellow solution. A solution of triphenylphosphine (1.14 g, 4.36 mmol) in carbon tetrachloride (15 ml) was added, causing the mixture to become an orange suspension- This was heated to reflux for 1.5 hours by which time TLC showed no remaining starting material. The reaction was allowed to cool to room temperature, and the orange solid was collected by filtration, washed with further CCl$_4$ and dried to give the product (0.54 g, 73%); δH [$^2$H$_6$]-DMSO 10.95 (1H, br s, 1-NH), 10.58 (1H, s, 5-NH), 8.25 (1H, t, J 5, amide NH), 8.10 (1H, d, J 9, 9-H), 7.88 (1H, s, 10-H), 7.29–7.46 (2H, m, 6-H, 7-H), 7.08 (1H, t, J 7.5, 8-H), 3.80 (2H, t, J 6, 2'-CH$_2$), 3.57–3.70 (2H, m, 1'-CH$_2$), 2.90 and 2.85 (2×3H, 2×s, 3-CH$_3$ and 4-CH$_3$); m/z (%) 304 (25, M+$^1$ $^+$); $v_{max}$ (KBr disc)/cm$^{-1}$ 1622, 1329.

N-(2-Chloroethyl) 3,4-dimethylpyrrolo[3,2-b]carbazole-2-carboxamide (0.15 g, 0.44 mmol) in ethanol (10 ml) was heated to reflux and 10M sodium hydroxide (88 μl, 0.88 mmol) was added. Reflux was continued for one minute then water (80 ml) was added and the mixture allowed to stand at room temperature for 2 hours. The resulting precipitate was filtered off, washed well with water, dried and crystallised from ethyl acetate/60–80 petrol to give the title compound as orange crystals (0.05 g, 37%) with m.p. 244° C. (decomp.) (Found: C, 75.30; H, 5.64; N, 13.67. C$_{19}$H$_{17}$N$_3$O requires: C, 75.23; H, 5.65; N, 13.85%); δH [$^2$H$_6$]-DMSO 11.03 (1H, s, 1-NH), 10.56 (1H, s, 5-NH), 8.04 (1H, d, J 7.5, 9-H), 7.83 (1H, s, 10-H), 7.45–7.30 (2H, m, 6-H, 7-H), 7.12–7.03 (1H, m, 8-H), 4.49–4.37 (2H, m, 4'-CH$_2$), 4.09–3.96 (2H, m, 5'-CH$_2$), 2.90 and 2.87 (2×3H, 2×s, 3-CH$_3$ and 4-CH$_3$); m/z (%) 303 (88, M$^+$), 259 (92), 246 (82), 231 (41), 217 (100), 204 (78); $v_{max}$ (KBr disc)/cm$^{-1}$ 3346, 3138, 1720, 1637.

EXAMPLE 16

3,4-Dimethyl-2-[3-(1-piperidinylmethyl)-1,2,4-oxadiazol-5-yl]pyrrolo[3,2-b]carbazole 3,4-Dimethylpyrrolo[3,2-b]carbazole-2-carboxylic acid (0.556 g, 2 mmol), (prepared as described in WO93/01512) and carbonyl diimidazole (0.37 g, 2.2 mmol) were dissolved in freshly distilled tetrahydrofuran (10 ml) in an oven-dried flask under a nitrogen atmosphere. The resulting orange solution was stirred at room temperature for three hours, by which time it was an orange suspension, and complete conversion of the acid to the imidazolide intermediate was verified by TLC. Meanwhile, in a second oven-dried flask, 2-(1-piperidino)acetamidoxime (0.692 g, 4.4 mmol) was dissolved in THF (10 ml). To this was added crushed 3 Å sieves (0.66 g) and the mixture was stirred at room temp for 1 hour. Sodium hydride (60% dispersion in mineral oil, 0.161 g, 4 mmol) was added and the mixture stirred for a further 2 hours. The contents of the two flasks were combined and stirred at room temp for 18 hours, by which time TLC showed complete consumption of the imidazolide intermediate. The solvent was removed in vacuo to give a yellow solid. Chromatography on silica (eluting with ethyl acetate/petrol, gradient 10%–27.5% ethyl acetate) gave a yellow solid (0.3 g, 37%). Crystallisation from ethyl acetate/petrol gave the title compound as yellow crystals of m.p. >201° C. (decomp.) (Found: C, 71.58; H, 6.28; N, 17.21. C$_{24}$H$_{25}$N$_5$O.0.2H$_2$O requires: C, 71.51; H, 6.35; N, 17.37%); δH [$^2$H$_6$]-DMSO 11.75 (1H, s, 1-NH), 10.68 (1H, s, 5-NH), 8.10 (1H, d, J 7.5, 9-H), 7.90 (1H, s, 10-H), 7.48–7.32 (2H, m, 6-H, 7-H), 7.09 (1H, ddd, J 7.5, 5.5, 2, 8-H), 3.70 (2H, s, 3'-CH$_2$N), 2.98 and 2.93 (2×3H, 2×s, 3-CH$_3$ and 4-CH$_3$), 2.58–2.48 (4H, m, piperidine CH$_2$, 6-CH$_2$, 1.62–1.34 (6H, m, piperidine 3-CH$_2$, 4-CH$_2$, 5-CH$_2$); m/z (%) 399 (4, M$^+$), 302 (44), 260 (100), 232 (46); $v_{max}$ (KBr disc)/cm$^{-1}$ 3365, 2937, 1603, 1331.

EXAMPLE 17

3,4-Dimethyl-2-[3-(4-pyridyl)-1,2,4-oxadiazol-5-yl] pyrrolo[3,2-b]carbazole 3,4-Dimethylpyrrolo[3,2-b]carbazole-2-carboxylic acid (0.556 g, 2 mmol), (prepared as described in WO93/01512) and carbonyl diimidazole (0.37 g, 2.2 mmol) were dissolved in freshly distilled tetrahydrofuran (10 ml) in an oven-dried flask under a nitrogen atmosphere. The resulting orange solution was stirred at room temperature for 2 hours, by which time it was an orange suspension, and complete conversion of the acid to the imidazolide intermediate was verified by TLC. Meanwhile, in a second oven-dried flask, 4-pyridylamidoxime (0.557 g, 4.1 mmol) was dissolved in THF (20 ml). To this was added crushed 3 Å sieves (0.66 g) and the mixture was stirred at room temp for 1 hour. Sodium hydride (60% dispersion in mineral oil, 0.161 g, 4 mmol) was added and the mixture stirred for a further 1 hour. The contents of the two flasks were combined and stirred at room temp for 18 hours, by which time TLC showed complete consumption of the imidazolide intermediate. The yellow precipitate which had formed was filtered off and taken up into hot DMSO. This was filtered and water was added. On cooling, yellow crystals of the title compound formed, were filtered off and dried (vacuum oven/85° C.) (0.265 g, 35%) m.p. >300° C. (decomp.) (Found: C, 71.37; H, 4.49; N, 17.94. C$_{23}$H$_{17}$N$_5$O.0.4H$_2$O requires: C, 71.45; H, 4.64; N, 18.11%); δH [$^2$H$_6$]-DMSO 11.85 (1H, s, 1-NH), 10.70 (1H, s, 5-NH), 8.17 and 8.05 (4H, AB quart, J 5.5, pyridine), 8.13 (1H, d, J 7.5, 9-H), 7.95 (1H, s, 10-H), 7.48–7.32 (2H, m, 6-H, 7-H), 7.10 (1H, ddd, J 7.5, 5.5, 2, 8-H), 3.08 and 2.95 (2×3H, 2×s, 3-CH$_3$ and 4-CH$_3$); m/z (%) 379 (5, M$^+$), 259 (42), 224 (61), 193 (100); ν$_{max}$ (KBr disc)/cm$^{-1}$ 3439, 3244, 1610, 1500, 1414, 1371, 1311, 1242.

EXAMPLE 18

3,4-Dimethyl-2-(3-methoxymethyl-1,2,4-oxadiazol-5-yl)pyrrolo[3,2-b]carbazole

Methoxymethylamidoxime

Sodium methoxide solution (sodium 7.88 g, 0.34 gatom in methanol (160 ml)) was added dropwise over 20 mins to hydroxylamine hydrochloride (23.63 g, 337.6 mmol) in methanol (315 ml) and stirred at room temperature for one hour. The resulting precipitate (NaCl) was filtered off and the filtrate was treated with methoxyacetonitrile (24 g, 337.6 mmol). The mixture was stirred and heated to reflux overnight, cooled and evaporated under reduced pressure to an oil. This was taken up into ethyl acetate which was washed with water, dried (MgSO$_4$) and evaporated to a clear oil (9 g, 26%) which solidified on standing. δH (CDCl$_3$) 9.16 (1H, s, br, OH), 4.96 (2H, s, NH$_2$), 3.96 (2H, s, CH$_2$), 3.36 (3H, s, CH$_3$).

3,4-Dimethylpyrrolo[3,2-b]carbazole-2-carboxylic acid (0.556 g, 2 mmol), (prepared as described in WO93/01512) and carbonyl diimidazole (0.37 g, 2.2 mmol) were dissolved in freshly distilled tetrahydrofuran (10 ml) in an oven-dried flask under a nitrogen atmosphere. The resulting orange solution was stirred at room temperature for 2 hours, by which time it was an orange suspension, and complete conversion of the acid to the imidazolide intermediate was verified by TLC. Meanwhile, in a second oven-dried flask, methoxymethylamidoxime (0.458 g, 4.4 mmol) was dissolved in THF (10 ml). To this was added crushed 3 Å sieves (0.66 g) and the mixture was stirred at room temp for 1 hour. Sodium hydride (60% dispersion in mineral oil, 0.161 g, 4 mmol) was added and the mixture stirred for a further 1 hour. The contents of the two flasks were combined and stirred at room temp for 18 hours, by which time TLC showed complete consumption of the imidazolide intermediate. The solvent was removed in vacuo to give a yellow solid which was adsorbed onto silica and chromatographed on silica (eluting with ethyl acetate/petrol, gradient 15%–30% ethyl acetate). Impure fractions were crystallised from ethyl acetate/petrol and combined with the pure fractions to give the title compound as a yellow solid (0.35 g, 51%) with m.p. >218° C. (decomp.) (Found: C, 69.04; H, 5.31; N, 15.85. C$_{20}$H$_{18}$N$_4$O$_2$ requires: C, 69.35; H, 5.24; N, 16.17%); δH [$^2$H$_6$]-DMSO 11.75 (1H, s, 1-NH), 10.68 (1H, s, 5-NH), 8.12 (1H, d, J 7.5, 9-H), 7.91 (1H, s, 10-H), 7.48–7.32 (2H, m, 6H, 7-H), 7.10 (1H, ddd, J 7.5, 5.5, 2, 8-H), 4.67 (2H, s, CH$_2$OCH$_3$), 3.43 (3H, s, CH$_2$OCH$_3$) 3.00 and 2.95 (2×3H, 2×s, 3-CH$_3$ and 4-CH$_3$); m/z (%) 347 (15, M+1$^+$), 274 (95), 257 (80), 232 (100); ν$_{max}$ (KBr disc)/cm$^{-1}$ 3373, 3338, 1603, 1497, 1315, 1238, 744.

EXAMPLE 19

3,4-Dimethyl-2-[3-(2-hydroxyethyl)-1,2,4-oxadiazol-5yl]pyrrolo[3,2-b]carbazole

3-tert-Butyldiphenylsilyloxyproprionitrile

3-Hydroxyproprionitrile (7.11 g, 100 mmol) and imidazole (68.08 g, 100 mmol) in dry THF (100 ml) was stirred at room temperature for 45 mins and tert-butyldiphenylsilylchloride (28.86 g, 105 mmol) was added slowly by syringe over 10 mins. The clear solution was stirred at room temperature overnight during which time a white precipitate formed. The reaction was filtered and the filtrate evaporated in vacuo to leave an oil which was chromatographed on silica (eluting with 10% petrol in ether) to give the product as a clear slightly yellow oil (31.41 g, quant.) δH (CDCl$_3$) 7.76–7.65 (4H, m, PhH$_4$), 7.48–7.35 (6H, m, PhH$_6$), 3.86 (2H, t, J 6.5, OCH$_2$CH$_2$CN), 2.54 (2H, t, J 6.5, OCH$_2$CH$_2$CN), 1.09 (9H, s, tert-Bu).

3-tert-Butyldiphenylsilyloxyethylamidoxime

A solution of sodium (2.33 g, 0.102 gatom) in dry methanol (50 ml) was added over 10 mins to hydroxylamine hydrochloride (7 g, 100 mmol) in dry methanol (50 ml) and the mixture was stirred at room temperature for one hour. The precipitate of sodium chloride was filtered off and the filtrate was added dropwise over 10 mins to a stirred solution of 3-tert-butyldiphenylsilyloxyproprionitrilei (31.08 g, 100 mmol) in dry methanol (50 ml). The mixture was stirred and heated at reflux overnight. After cooling, the methanol was evaporated in vacuo and the residue partitioned between ethyl acetate and water. The aqueous phase was separated and extracted several times with ethyl acetate. The combined ethyl acetate phases were dried (MgSO$_4$) and evaporated in vacuo to a pale yellow oil which was chromatographed on silica (eluting with ethyl acetate/petrol, gradient 20%–100% ethyl acetate) to give unreacted nitrile (14.75 g, 47%) and the product as a viscous, clear, yellow oil (12.54 g, 37%) δH (CDCl$_3$) 7.72–7.62 (4H, m, PhH$_4$), 7.46–7.32 (6H, m, PhH$_6$), 5.05 (2H, s, br, NH$_2$), 3.88 (2H, t, J 6.5, OCH$_2$CH$_2$), 2.38 (2H, t, J 6.5, OCH$_2$CH$_2$), 1.07 (9H, s, tert-Bu).

3,4-Dimethyl-2-[3-(2-tert-butyldiphenylsilyloxyethyl)-1,2,4-oxadiazol-5-yl]pyrroloo3,2-b]carbazole 3,4-Dimethylpyrrolo[3,2-b]carbazole-2-carboxylic acid (1.12 g, 4 mmol), (prepared as described in WO93/01512) and carbonyl diimidazole (0.74 g, 4.4 mmol) were dissolved in freshly distilled tetrahydrofuran (20 ml) in an oven-dried flask under a nitrogen atmosphere. The resulting orange solution was stirred at room temperature for 2.5 hours, by which time it was an orange suspension, and complete conversion of the acid to the imidazolide intermediate was verified by TLC. Meanwhile, in a second oven-dried flask, 3-tert-Butyldiphenylsilyloxyethylamidoxime (3.014 g, 8.8 mmol) was dissolved in THF (20 ml). To this was added crushed 3 Å sieves (1.32 g) and the mixture was stirred at room temp for one hour. Sodium hydride (60% dispersion in mineral oil, 0.354 g, 8.8 mmol) was added and the mixture stirred for a further 1.5 hours. The contents of the two flasks were combined and stirred at room temp for 18 hours, by which time TLC showed complete consumption of the imidazolide intermediate. The solvent was removed in vacuo to give a solid which was adsorbed onto silica and chromatographed on silica (eluting with ethyl acetate/petrol, gradient 7%–8% ethyl acetate) to give a yellow solid (0.382 g, 16%) δH [$^2$H$_6$]-DMSO 11.70 (1, s, 1-NH), 10.68 (1H, s, 5-NH), 8.11 (1H, d, J 7.5, 9-H), 7.92 (1H, s, 10-H), 7.66–7.57 (4H, m, PhH$_4$), 7.48–7.32 (8H, m, 6H, 7-H, PhH6), 7.15–7.04 (1H, n, 8-H), 4.13 (2H, t, J 6.5, OCH$_2$CH$_2$), 3.10 (2H, t, J 6.5, OCH$_2$CH$_2$), 3.00 and 2.96 (2×3H, 2×s, 3-CH$_3$ and 4-CH$_3$), 0.96 (9H, s, tert-Bu).

Tetra-n-butylammonium fluoride (1M in THF, 1.9 ml, 1.9 mmol) was added to a stirred solution of 3,4-dimethyl-2-

[3-(2-tert-butyldiphenylsilyloxyethyl)-1,2,4-oxadiazol-5-yl] pyrrolo[3,2-b]carbazole (0.36 g, 0.616 mmol) in THF (20 ml). The reaction was stirred at room temperature overnight then partitioned between ethyl acetate and water. The aqueous phase was separated and extracted several times with ethyl acetate. The combined ethyl acetate phases were dried (MgSO$_4$) and evaporated in vacuo to give a solid which was adsorbed onto silica and chromatographed on silica (eluting with ethyl acetate/petrol, gradient 25%–50% ethyl acetate) giving the title compound as a yellow solid (0.155 g, 70%) with m.p. 232°–234° C. (decomp.) (Found: C, 68.18; H, 5.36; N, 15.01. C$_{20}$H$_{18}$N$_4$O$_2$.0.25 EtOAc requires: C, 68.46; H, 5.47; N, 15.21%); δH [$^2$H$_6$]-DMSO 11.68 (1H, s, 1-NH), 10.67 (1H, s, 5-NH), 8.11 (1H, d, J 7.5, 9-H), 7.91 (1H, s, 10-H), 7.47–7.32 (2H, m, 6-H, 7-H), 7.14–7.03 (1H, m, 8-H), 4.86 (1H, t, J 6, OH), 3.87 (2H, t, J 6.5, HOC H$_2$CH$_2$), 2.99 (3H, s, 3-CH$_3$ or 4-CH$_3$), 2.98–2.91 (5H, m, 3-CH$_3$ or 4-CH$_3$, OCH$_2$CH$_2$); m/z (%) 347 (100, M+1$^+$), 302 (15), 278 (68); $\nu_{max}$ (Kbr disc)/cm$^{-1}$ 3334, 1705, 1595.

EXAMPLE 20

2-(3-Ethyl-1,2,4-oxadiazol-5-yl)-4-methyl-1H-[1] benzofuro[2,3-ƒ]indole

4-Methyldibenzofuran

Dibenzofuran (26.94 g, 160 mmol) was dissolved in dry THF (500 ml) and cooled to −78° C. n-Butyl lithium (1.6M in hexane, 200 ml, 320 mmol) was added in portions over 30 mins. and the solution was allowed to warm to room temperature over 2.5 hours. The solution was recooled to −70° C. and a mixture of dimethyl sulphate (32 ml, 340 mmol) in dry THF (100 ml) was added dropwise. Once the addition was complete, the reaction was allowed to warm to room temperature, stirred for 18 hours and poured onto saturated ammonium chloride solution (400 ml). The phases were separated and the aqueous extracted twice with ether. The combined organic phases were dried (MgSO$_4$) and evaporated in vacuo. Chromatography on silica (eluting with 40–60 petrol) gave the pure product as a clear oil (29.2 g, 100%) δH [$^2$H$_6$]-DMSO 8.1 (1H, d), 7.9 (1H, d), 7.7 (1H, d),7.5 (1H, t), 7.4 (1H, t), 7.25 (2H, m), 2.55 (3H, s).

3-Bromo4-methyldibenzofuran

4-Methyldibenzofuran (30 g, 165 mmol) and sodium carbonate (17.5 g, 165 mmol) were mixed in hexane (300 ml) and bromine (26.4 g, 165 mmol) was added. The reaction was stirred at room temperature for 72 hours, then the solvent was removed in vacuo to give an oil which crystallised. Recrystallisation from IMS yielded several batches of off-white crystals (31.22 g, 72%) with m.p. 124°–125° C. (Found: C, 58.59; H, 3,28. C$_{13}$H$_9$BrO 0.31H$_2$O requires: C, 58.58; H, 3.63%); δH [$^2$H$_6$]-DMSO 8.15 (1H, d), 7.9 (1H, d), 7.7 (1H, d), 7.4 (1H, t), 7.05 (2H, m), 2.6 (3H, s); m/z 260/262 (M$^+$).

4-Methyldibenzofuran-3-carboxaldehyde

3-Bromo4-methyldibenzofuran (26.11 g, 0.1 mol) suspended in dry ether (700 ml) was cooled to 0° C. and n-butyl lithium (1.6M in hexane, 62.5 ml, 0.1 mol) was added and the reaction stirred for 5 mins. DMF (5 ml) in ether (12 ml) was added and the reaction heated to reflux for 1 hour. The mixture was poured onto a mixture of conc. HCl (25 ml) and ice (1 l). The organic phase was separated and the aqueous extreacted with ether. The combined organic phases were dried (MgSO$_4$) and evaporated in vacuo. The resulting solid was crystallised from IMS to give off-white needles which were dried at 60° C. under vacuum (4.68 g, 22%). Further product could be obtained from the mother liquor. (Found: C, 78.97; H, 4.56. C$_{14}$H$_{10}$O$_2$ 0.15H$_2$O requires: C, 78.97; H, 4.88%); δH [$^2$H$_6$]-DMSO 10.4 (1H, s, CHO), (8.2 (1H, d), 8.15 (1H, d), 7.9 (1H, d), 7.8 (1H, d), 7.65 (1H, t), 7.45 (1H, t), 2.85 (3H, s); m/z 210 (M$^+$); $\nu_{max}$ (KBr disc)/cm$^{-1}$ 1686.

Ethyl 4-methyl-1H-[1]-Benzofuro[2,3-ƒ]indole-2-carboxylate

A mixture of 4-methyldibenzofuran-3-carboxaldehyde (3.9 g, 18.6 mmol) and ethyl azidoacetate (12.5 g, 97 mmol) in dry THF (15 ml) was added dropwise to a solution of sodium (1.7 g, 0.074 gatom) in absolute ethanol (200 ml) stirred at 0° C. The mixture was stirred at 0° C. for 2 hours then kept at −20° C. for 72 hours. The yellow precipitate formed was filtered off, washed with a little ice-cold ethanol and dissolved as far as possible in ether. The ether was filtered and the filtrate evaporated in vacuo. The resulting yellow solid was dried for 18 hours under vacuum at room temperature before being added in portions over 10 mins. to xylene (300 ml) heated to reflux. Reflux was continued for 20 mins, after which the mixture was cooled slightly and filtered. The solid residue was washed with toluene. The filtrate and washings were evaporated in vacuo to leave an orange semi-solid. This was chromatographed on silica (eluting with ethyl acetate/petrol, gradient 0–20% ethyl acetate) to give the product as a cream solid (1.25 g, 23%) which was crystallised from petrol to give white crystals with m.p. 178°–179° C. (Found: C, 73,41; H, 5.12; N, 4.75.C$_{18}$H$_{15}$NO$_3$ requires: C, 73.71, H, 5.15; N, 4.78%); δH [$^2$H$_6$]-DMSO 12.0 (1H, b, NH), 8.2 (1H, d), 7.9 (1H, s), 7.65 (1H, d), 7.5 (1H, t), 7.45 (2H, m), 4.4 (2H, q), 2.7 (3H, s), 1.4 (3H, t); m/z 293 (M$^+$); $\nu_{max}$ (KBr disc)/cm$^{-1}$ 3339, 1682.

4-Methyl-1H-[1]-benzofuro[2,3-ƒ]indole-2-carboxylic acid

Ethyl 4-methyl-1H-[1]-benzofuro[2,3-ƒ]indole-2-carboxylate (0.105 g, 0.36 mmol) was suspended in water (3 ml) and methanol (11 ml). Cesium carbonate (1.0 g, 3.1 mmol) was added and the reaction was heated to reflux for one hour. The methanol was evaporated in vacuo and the remaining aqueous solution was acidified with 0.1M hydrochloric acid. The white precipitate was filtered off and washed with water to give a pale yellow solid (0.075 g, 79%); δH [$^2$H$_6$]-DMSO 13.0 (1H, b, COOH), 11.9 (1H, b, NH), 8.15 (1H d), 7.9 (1H, s), 7.55 (1H, d), 7.5 (1H, t), 7.35 (2H, m), 2.7 (3H, s).

4-Methyl-1H-[1]-benzofuro[2,3-ƒ]indole-2-carboxylic acid (1.0 g, 3.8 mmol) and carbonyl diimidazole (0.7 g, 4.3 mmol) were dissolved in freshly distilled tetrahydrofuran (40 ml) in an oven-dried flask under a nitrogen atmosphere. The resulting orange solution was stirred at room temperature for 2 hours, by which time it was an orange suspension, and complete conversion of the acid to the imidazolide intermediate was verified by TLC. Meanwhile, in a second oven-dried flask, ethylamidoxime (0.9 g, 10.2 mmol) was dissolved in THF. To this was added crushed 3 Å sieves (1.25 g) and the mixture was stirred at room temp for 1 hour. Sodium hydride (60% dispersion in mineral oil, 0.31 g, 7.8 mmol) was added and the mixture stirred for a further 1 hour. The contents of the two flasks were combined and stirred at room temp for 18 hours, by which time TLC showed complete consumption of the imidazolide intermediate. The solvent was removed in vacuo and the residue was chromatographed on silica (eluting with 10% ethyl acetate/ toluene) to give the title compound as a yellow solid (0.775 g, 64%) with m.p. 191°–192° C. (Found: C, 71.86; H, 4.77; N, 13.18. $C_{19}H_{15}N_3O_2$ requires: C, 71.91; H, 4.76; N, 13.24%); δH [$^2H_6$]-DMSO 12.5 (1H, b, NH), 8.2 (1H, d), 8.0 (1H, s), 7.65 (1H, d), 7.6 (1H, s), 7.5 (1H, t), 7.4 (1H, t), 2.85 (2H, q), 2.75 (3H, s), 1.35 (3H, t); m/z 317 (M$^+$); $v_{max}$ (KBr disc)/cm$^{-1}$ 3244.

EXAMPLE 21

3,4-Dimethyl-2-(4,4-dimethyl-2-oxazolin-2-yl) pyrrolo[3,2-b]carbazole

N-(2-Hydroxymethyl-2-propyl-2)3,4-dimethylpyrrolo[3,2-b]carbazole-2-carboxamide 3,4-Dimethylpyrrolo[3,2-b]carbazole-2-carboxylic acid (0.556 g, 2.0 mmol) was weighed into an oven-dried flask under nitrogen and dissolved in DMF (10 ml). Carbonyl diimidazole (0.37 g, 2.2 mmol) was added and the mixture stirred at room temperature for 2.5 hours, by which time TLC showed no remaining starting material. 2-Amino-2-methylpropanol (25 g, excess) was added and the resulting mixture was heated to 75°–80° C. for 4 hours, by which time TLC showed no remaining imidazolide intermediate. Water (300 ml) was added, giving an orange precipitate, which was collected by filtration, washed with water and dried. This solid was recrystallised from DMF/water to give the product (0.216 g, 31%) with m.p. 210° C. (decomp.); δH [$^2H_6$]-DMSO 10.96 (1H, br s, 1-NH), 10.57 (1H, s, 5-NH), 8.09 (1H, d, J 9, 9-H), 7.83 (1H, s, 10-H), 7.29–7.47 (2H, m, 6-H, 7-H), 7.19 (1H, br s, amide NH), 7.08 (1H, t, J 7.5, 8-H), 4.99 (1H, t, J 5.5, O-H), 3.58 (2H, d, J 5.5, 2'-H2), 2.89 and 2.80 (2×3H, 2×s, 3-CH$_3$ and 4-CH$_3$), 1.39 (6H, s, C(CH$_3$)$_2$); m/z (%) 349 (65, M$^+$), 261 (80), 181 (90), 149 (93), 57 (100); $v_{max}$ (KBr disc)/cm$^{-1}$ 3331, 1608, 1539, 1309, 1244; (Found: M$^+$349.1810, $C_{21}H_{23}N_3O_2$ requires 349.1790).

N-(2-Hydroxymethyl-2-propyl-2)3,4-dimethylpyrrolo[3,2-b]carbazole-2-carboxamide (1 g, 2.87 mmol) and triphenylphosphine (1.6 g; 6.1 mmol) were heated to reflux in a mixture of CCl$_4$ (80 ml) and DMF (7.5 ml) for one hour. The resulting red solution was evaporated in vacuo to low volume then partitioned between toluene and water. The aqueous phase was separated and extracted several times with toluene. The combined organic phases were evaporated in vacuo and the residue was adsorbed onto silica prior to chromatography on silica (eluting with ethyl acetate/petrol, gradient 10%–20% ethyl acetate) to give a beige powder (0.19 g). Crystallisation from ethyl acetate yielded the title compound as a pale yellow solid with m.p. 223°–225° C. (decomp.) (Found: C, 75.33; H, 6.32; N, 12.33. $C_{21}H_{21}N_3O.0.22$ $H_2O$ requires: C, 75.21; H, 6.44; N, 12.53%); δH [$^2H_6$]-DMSO 11.00 (1H, s, 1-NH), 10.55 (1H, s, 5-NH), 8.03 (1H, d, J 7.5, 9-H), 7.85 (1H, s, 10-H), 7.46–7.28 (2H, m, 6-H, 7-H), 7.09 (1H, ddd, J 7.5, 5.5, 2, 8-H), 4.14 (2H, s, 5'-CH$_2$), 2.91 and 2.86 (2×3H, 2×s, 3-CH$_3$ and 4-CH$_3$ 1.35 (6H, s, 4'-(CH$_3$)$_2$); m/z (%) 331 (83, M$^+$), 316 (22), 259 (100); $v_{max}$ (KBr disc)/cm$^{-1}$ 3396, 2964, 1639, 1581, 1462.

EXAMPLE 22

3,4-Dimethyl-2-[3-(3-hydroxyphenyl)-1,2,4-oxadiazol-5-yl]pyrrolo[3,2-b]carbazole 3-(tert-Butyldiphenylsilyloxy)benzonitrile 3-Hydroxyphenylamidoxime (13.85 g, 116.3 mmol), tert-butyldiphenylsilylchloride (31 ml, 119.21 mmol) and DBU (17.88 g, 117.46 mmol) in DCM (550 ml) were stirred at room temperature overnight. The DCM solution was washed with water, sodium bicarbonate solution and brine, dried (MgSO$_4$) and evaporated in vacuo to leave a pale yellow oil which was chromatographed on silica (eluting with 3% ether in petrol) to give the product as a colourless oil (37.12 g, 89%) δH (CDCl$_3$) 7.73–6.88 (14H, m, Aromatic), 1.12 (9H, s, tert-Bu).

3-Hydroxyphenylamidoxime

Methanolic sodium methoxide prepared from sodium (2.42 g, 0.106 gatom) in methanol (50 ml) was added to hydroxylamine hydrochloride (7.27 g, 103.82 mmol) in methanol (100 ml). The mixture was stirred at room temperature for one hour then added to a solution of 3-(tert-Butyldiphenylsilyloxy)benzonitrile (37.12 g, 103.82 mmol) in methanol (50 ml). The reaction was heated to reflux overnight, cooled and evaporated in vacuo. The residue was partitioned between ethyl acetate and water and the aqueous phase was separated and extracted with ethyl acetate. The combined organic phases were dried (MgSO$_4$) and evaporated in vacuo to a gum which was chromatographed on silica (eluting with ethyl acetate/petrol, gradient 10%–100% ethyl acetate) to give the desilylated amidoxime as a white solid (13.46 g) δH [$^2H_6$]-DMSO 9.52 (1H, s, OH), 9.43 (1H, s, OH), 7.23–7.05 (3H, m, PhH$_3$), 6.80–6.73 (1H, n, PhH$_1$), 5.68 (2H, s, NH$_2$).

3,4-Dimethylpyrrolo[3,2-b]carbazole-2-carboxylic acid (0.556 g, 2 mmol), (prepared as described in WO93/01512) and carbonyl diimidazole (0.37 g, 2.2 mmol) were dissolved in freshly distilled tetrahydrofuran (10 ml) in an oven-dried flask under a nitrogen atmosphere. The resulting orange solution was stirred at room temperature for 2 hours, by which time it was an orange suspension, and complete conversion of the acid to the imidazolide intermediate was verified by TLC. Meanwhile, in a second oven-dried flask, 3-hydroxyphenylamidoxime (0.669 g, 4.4 mmol) was dissolved in THF (10 ml). To this was added crushed 3 Å sieves (0.66 g) and the mixture was stirred at room temp for 45 mins. Sodium hydride (60% dispersion in mineral oil, 0.176 g, 4.4 mmol) was added and the mixture stirred for a further 1 hour. The contents of the two flasks were combined and stirred at room temp for 18 hours, by which time TLC showed complete consumption of the imidazolide intermediate. The solvent was removed in vacuo to give a solid which was adsorbed onto silica and chromatographed on silica (eluting with ethyl acetate/petrol, gradient 5%–25% ethyl acetate) to give a mustard powder (0.167 g, 21%). Crystallisation from DMF/water gave the title compound as yellow/orange crystals with m.p. 255° C. (decomp.) (Found: C, 68.65; H, 5.24; N, 14.95. $C_{24}H_{18}N_4O_2$ .0.3 $H_2O$.0.9 DMF requires: C, 68.87; H, 5.39; N, 14.74%); δH [$^2H_6$]-DMSO 11.78 (1H, s, 1-NH), 10.69 (1H, s, 5-NH), 9.89 (1H, s, br, PhOH), 8.13 (1H, d, J 7.5, 9-H), 7.95 (1H, s, 10-H), 7.63–7.56 (2H, m, PhH$_2$), 7.48–7.32 (3H, m, 6-H, 7-H, PhH$_1$), 7.16–6.98 (2H, m, 8-H, PhH$_1$), 3.07 and 2.95 (2×3H, 2×s, 3-CH$_3$ and 4-CH$_3$); m/z (%) 394 (92, M$^+$295 (28), 260 (100), 231 (68); $v_{max}$ (KBr disc)/cm$^{-1}$ 3342, 1670, 1603, 1377, 1335, 1238.

EXAMPLE 23

3,4-Dimethyl-2-[3-(N,N-dimethylaminomethyl)-1,2,4-oxadiazol-5-yl]pyrrolo[3 2-b]carbazole 2-N,N-Dimethylamino)acetamidoxime Sodium (3.77 g, 0.164 gatom) was added in aliquots to hydroxylamine hydrochloride (11.44 g, 163,46 mmol) in butan-1-ol (250 ml) while heated and stirred at 80° C. On completion of the addition the solution was allowed to cool and was stirred for two hours. The precipitated sodium chloride was filtered off and dimethylaminoacetonitrile (14.48 ml, 148.60 mmol) was added. The reaction was stirred at 40° C. for 21 hours, partially evaporated in vacuo and cooled. The product crystallised as white crystals which were filtered, washed with butan-1-ol, then petrol and dried overnight at 65° C. under vacuum (7.4 g, 42%) with m.p. 112°–114° C. (Found: C, 40.83; H, 9.50; N, 35.74. $C_4H_{11}N_3O$ requires: C, 41.01; H, 9.46; N, 35.87%); δH [$^2H_6$]-DMSO 8.92 (1H, s, OH), 5.17 (2H, s, $NH_2$), 2.75 (2H, s, $CH_2$), 2.13 (6H, s, 2×$CH_3$).

3,4-Dimethylpyrrolo[3,2-b]carbazole-2-carboxylic acid (0.556 g, 2 mmol), (prepared as described in WO93/01512) and carbonyl diimidazole (0.37 g, 2.2 mmol) were dissolved in freshly distilled tetrahydrofuran (10 ml) in an oven-dried flask under a nitrogen atmosphere. The resulting orange solution was stirred at room temperature for 2 hours, by which time it was an orange suspension, and complete conversion of the acid to the imidazolide intermediate was verified by TLC. Meanwhile, in a second oven-dried flask, 2-(N,N-dimethylamino)acetamidoxime (0.515 g, 4.4 mmol) was dissolved in THF (10 ml). To this was added crushed 3 Å sieves (0.66 g) and the mixture was stirred at room temp for 45 mins. Sodium hydride (60% dispersion in mineral oil, 0.176 g, 4.4 mmol) was added and the mixture stirred for a further 1 hour. The contents of the two flasks were combined and stirred at room temp for 18 hours, by which time TLC showed complete consumption of the imidazolide intermediate. The solvent was removed in vacuo to give a solid which was adsorbed onto silica and chromatographed on silica (eluting with ethyl acetate/petrol, gradient 20%–60% ethyl acetate) to give the title compound as a yellow powder (0.4 g, 45%) with m.p. >203° C. (decomp.) (Found: C, 69.26; H, 5.85; N, 18.89. $C_{21}H_{21}N_5O.0.33 H_2O$ requires: C, 69.03; H, 5.98; N, 19.17%); δH [$^2H_6$]-DMSO 11.70 (1H, s, 1-NH), 10.65 (1H, s, 5-NH), 8.10 (1H, d, J 7.5, 9-H), 7.90 (1H, s, 10-H), 7.43–7.28 (2H, m, 6-H, 7-H), 7.10 (1H, ddd, J 7.5, 5.5, 2, 8-H), 3.70 (2H, s, 3'-$CH_2N$), 3.00 and 2.95 (2×3H, 2×s, 3-$CH_3$ and 4-$CH_3$), 2.33 (6H, s, $N(CH_3)_2$); m/z (%) 359 (10, M$^+$), 302 (22), 260 (62), 232 (28); $v_{max}$ (Kbr disc)/cm$^{-1}$ 3385, 1593, 1572, 1462, 1391, 1309, 1240.

EXAMPLE 24

3,4-Dimethyl-2-(tetrazol-5-yl)pyrrolo[3,2-b]carbazole)

3,4-Dimethylpyrrolo[3,2-b]carbazole-2-carboxamide 3,4-Dimethyl-2-(hydrazinocarbonyl)Ipyrrolo[3,2-b] carbazole (2.92 g, 10 mmol) (prepared as described in WO93/01512) was suspended in methanol (650 ml) and stirred at 0° to 5° C. while 0.1M samarium iodide in THF (400 ml, 40 mmol) was added over four hours. After 1.5 hours stirring at the same temperature, methanol (100 ml) was added and the reaction was quenched with saturated ammonium chloride (100 ml). After warming to room temperature, the mixture was filtered through a pad of silica which was washed well with methanol. The combined filtrate and washings were concentrared in vacuo to remove the organic solvents. Water (300 ml) was added and after standing at room temperature for 2 hours the product was filtered off, washed well with water and and dried in the air to give a yellow solid (2.61 g, 94%) which was spectroscopically identical to previously reported material (WO/01512).

2-Cyano-3,4-dimethylpyrrolo[3 2-b]carbazole 3,4-Dimethylpyrrolo[3,2-b]carbazole-2-carboxamide (1 g, 3.61 mmol) suspended in dioxane was stirred and cooled to 15° C. Pyridine (2.9 ml, 36.1 mmol) was added followed by trifluoroacetic anhydride (2.5 ml, 18.1 mmol) in dioxane (10 ml) over 20 minutes. After a further one hour of stirring, the reaction was poured onto saturated sodium bicarbonate solution (400 ml) and stirred for 10 minutes prior to filtering off an orange solid which was washed well with water, dried under vacuum at room temperature and crystallised from ethyl acetate/60–80 petrol to give the product as an orange solid (0.54 g, 57%) with m.p. 215° C. (decomp.). (Found: C, 71.16; H, 4.46; N, 13.17. $C_{17}H_{13}N_3$.0.21 TFA.0.09EtOAc requires: C, 70.88; H, 4.74; N, 13.45%) δH [$^2H_6$]-DMSO 11.69 (1H, s, 1-NH), 10.72 (1H, s, 5-NH), 8.13 (1H, d, J 7.5, 9-H), 7.90 (1H, s, 10-H), 7.48–7.34 (2H, m, 6-H, 7-H), 7.09 (1H, ddd, J 7.5, 5.5, 2, 8-H), 2.88 and 2.73 (2×3H, 2×s, 3-$CH_3$ and 4-$CH_3$); m/z 259 (M$^+$); $v_{max}$ (KBr disc)/cm$^{-1}$ 3373, 3359, 2218, 1686.

2-Cyano-3,4-dimethylpyrrolo[3,2-b]carbazole (0.096 g, 0.37 mmol) and sodium azide (0.121 g, 1.86 mmol) were added to a solution of trimethyltin chloride (0.37 g, 1.86 mmol) in toluene (25 ml) and the resulting yellow suspension was heated to reflux for 48 hours. After cooling, filtering, washing and drying, the residual cream-coloured solid (0.09 g) was stirred in a mixture of toluene (10 ml) and THF (2 ml) and the mixture was saturated with HCl gas to form an orange suspension. After stirring for 15 minutes at room temperature, then 0° C., the precipitate was filtered off, dried and crystallised from ethanol (15 ml) to which was added water (75 ml) to yield the title compound (0.029 g, 26%) with m.p. 226° C. (decomp.). δH [$^2H_6$]-DMSO 11.12 (1H, s, 1-NH), 10.56 (1H, s, 5-NH), 8.28 (1H, s, tet-NH), 8.07 (1H, d, J 7.5, 9-H), 7.91 (1H, s, 10-H), 7.43–7.30 (2H, m, 6-H, 7-H), 7.09–7.03 (1H, m, 8-H), 2.93 and 2.88 (2×3H, 2×s, 3-$CH_3$ and 4-$CH_3$); $v_{max}$ (KBr disc)/cm$^{-1}$ 3427, 3244, 3061, 2924, 1603, 1572; (Found: M$^+$, 302.12998. $C_{17}H_{14}N_6$ requires 302.12799).

EXAMPLE 25

3,4-Dimethyl-2-[3-(4-morpholinomethyl)-1,2,4-oxadiazol-5-yl]pyrrolo[3,2-b]carbazole 2-(4-Morpholino)acetamidoxime A solution of sodium (3.51 g, 0.153 gatom) in methanol (70 ml) was added to hydroxylamine hydrochloride (10.5 g, 150 mmol) in methanol (140 ml) and stirred for one hour after which the precipitate of sodium chloride was filtered off. The filtrate was treated with 4-morpholinoacetonitrile (18.92 g, 150 mmol) and stirred and heated at 70° C. for 9 hours. Evaporation of the solvent in vacuo and crystallisation from methanol gave the product in two crops of colourless crystals (15.6 g, 65%) with m.p. 153°–155° C. (decomp.) (Found: C, 45.09; H, 8.35; N, 26.35. $C_6H_{13}N_3O_2$ requires: C, 45.27; H, 8.23; N, 26.40%) δH [$^2H_6$]-DSMO 8.97 (1H, s, OH), 5.21 (2H, s, $NH_2$), 3.62–3.55 (4H, mn, $CH_2OCH_2$), 2.83 (2H, s, 3'-$CH_2N$), 2.39–2.31 (4H, m, C $\underline{H}_2N(CH_2)C\underline{H}_2$).

3,4-Dimethylpyrrolo[3,2-b]carbazole-2-carboxylic acid (0.556 g, 2 mmol), (prepared as described in WO93/01512) and carbonyl diimidazole (0.37 g, 2.2 mmol) were dissolved in freshly distilled tetrahydrofuran (10 ml) in an oven-dried flask under a nitrogen atmosphere. The resulting orange solution was stirred at room temperature for 2 hours, by which time it was an orange suspension, and complete conversion of the acid to the imidazolide intermediate was verified by TLC. Meanwhile, in a second oven-dried flask, 2-(4-morpholino)acetamidoxime (0.7 g, 4.4 mmol) was dissolved in THF (10 ml). To this was added crushed 3 Å sieves (0.66 g) and the mixture was stirred at room temp for 25 mins. Sodium hydride (60% dispersion in mineral oil, 0.176 g, 4.4 mmol) was added and the mixture stirred for a further 1½ hours. The contents of the two flasks were combined and stirred at room temp over the weekend, by which time TLC showed complete consumption of the imidazolide intermediate. The solvent was removed in vacuo to give a solid which was dissolved in hot methanol and filtered. Addition of water precipitated an impure yellow solid which which was filtered off and chromatographed on silica (eluting with ethyl acetate/petrol, gradient 35%–60% ethyl acetate) to give a yellow powder (0.145 g, 18%). Crystallisation from DMF/water gave the title compound as a yellow powder with m.p. 190°–205° C. (decomp.) (Found: C, 68.63; H, 5.77; N, 17.20. $C_{23}H_{23}N_5O_2$ requires: C, 68.81; H, 5.77; N, 17.44%); δH [$^2H_6$]-DMSO 11.68 (1H, s, 1-NH), 10.62 (1H, s, 5-NH), 8.08 (1H, d, J 7.5, 9-H), 7.90 (1H, s, 10-H), 7.43–7.32 (2H, m, 6-H, 7-H), 7.12–7.05 (1H, m, 8-H), 3.77 (2H, s, 3'-CH$_2$N), 3.64–3.58 (4H, m, CH$_2$OCH$_2$), 3.00 and 2.95 (2×3H, 2×s, 3-CH$_3$ and 4-CH$_3$), 2.60–2.65 (4H, m, C$\underline{H}_2$N(CH$_2$)C$\underline{H}_2$); m/z (%) 401 (8, M$^+$), 302 (21), 277 (16), 260 (100), 232 (50); $v_{max}$ (KBr disc)/cm$^{-1}$ 3363, 1593, 1570, 1491, 1329, 1309, 1242.

EXAMPLE 26

3,4-Dimethyl-2-(3-methoxyethyl-1,2,4-oxadiazol-5-yl)pyrrolo[3,2-b]carbazole

3-Methoxyethylamidoxime

A solution of sodium (7.88 g, 0.343 gatom) in methanol (160 ml) was added to hydroxylamine hydrochloride (23.63 g, 337.6 mmol) in methanol (315 ml) and stirred for 30 mins after which the precipitate of sodium chloride was filtered off. The filtrate was treated with 3-methoxyproprionitrile (28.73 g, 337.6 mmol) and stirred and heated at reflux overnight. The solvent was evaporated in vacuo and the residual oil was partitioned between ethyl acetate and water. The aqueous phase was extracted with ethyl acetate and the combined organic phases were evaporated in vacuo to leave an orange oil which was chromatographed on silica (eluting with ethyl acetate/petrol, gradient 50%–100% ethyl acetate) to give the product as a yellow oil (16 g, 40%) δH (CDCl$_3$) 8.6 (1H, br, OH), 4.94 (2H, s, br, NH$_2$), 3.58 (2H, t, J 8, CH$_2$C$\underline{H}_2$OCH$_3$), 3.36 (3H, s, CH$_2$CH$_2$OCH$_3$), 3.36 (3H, s, CH$_2$CH$_2$OC$\underline{H}_3$), 2.39 (2H, t, J 8, C$\underline{H}_2$CH$_2$OCH$_3$).

3,4-Dimethylpyrrolo[3,2-b]carbazole-2-carboxylic acid (0.556 g, 2 mmol), (prepared as described in WO93/01512) and carbonyl diimidazole (0.37 g, 2.2 mmol) were dissolved in freshly distilled tetrahydrofuran (10 ml) in an oven-dried flask under a nitrogen atmosphere. The resulting orange solution was stirred at room temperature for 2 hours, by which time it was an orange suspension, and complete conversion of the acid to the imidazolide intermediate was verified by TLC. Meanwhile, in a second oven-dried flask, 3-methoxyethylamidoxime (0.52 g, 4.4 mmol) was dissolved in TH (10 ml). To this was added crushed 3 Å sieves (0.66 g) and the mixture was stirred at room temp for one hour. Sodium hydride (60% dispersion in mineral oil, 0.176 g, 4.4 mmol) was added and the mixture stirred for a further one hour. The contents of the two flasks were combined and stirred at room temp overnight, by which time TLC showed complete consumption of the imidazolide intermediate. The solvent was removed in vacuo to give a solid which was adsorbed onto silica and chromatographed on silica (eluting with ethyl acetate/toluene, gradient 5%–9% ethyl acetate) to give a yellow solid. Crystallisation from DMF/water gave the title compound as a yellow crystals (0.303 g, 42%) with m.p. 240°–242° C. (decomp.) (Found: C, 69.90; H, 5.58; N, 15.39. $C_{21}H_{20}N_4O_2$ requires: C, 69.98; H, 5.59; N, 15.55%); δH [$^2H_6$]-DMSO 11.60 (1H, s, 1-NH), 10.59 (1H, s, 5-NH), 8.08 (1H, d, J 7.5, 9-H), 7.90 (1H, s, 10-H), 7.43–7.32 (2H, m, 6-H, 7-H), 7.12–7.03 (1H, m, 8-H), 3.80 (2H, t, J 8, CH$_2$C$\underline{H}_2$OCH$_3$), 3.30 (3H, s, OCH$_3$), 3.06 (2H, t, J 8, C$\underline{H}_2$CH$_2$OCH$_3$), 3.98 and 2.92 (2×3H, 2×s, 3-CH$_3$ and 4-CH$_3$); m/z (%) 360 (100, M$^+$), 328 (16), 315 (20), 260 (59), 231 (38); $v_{max}$ (KBr disc)/cm$^{-1}$ 3359, 1597, 1373, 1336, 1317, 1236.

EXAMPLE 27

3,4-Dimethyl-2-(1,2,4-oxadiazol-5-yl)pyrrolo[3,2-b]carbazole

Hydroxyaminomethylidene-(3,4-dimethylpyrrolo[3,2-b]carbazole-2-carboxamide)

Dimethylformamide dimethylacetal (1.91 ml, 14.4 mmol) was added to 3,4-dimethylpyrrolo[3,2-b]carbazole-2-carboxamide (0.2 g, 0.72 mmol) in toluene (30 ml) in a flask fitted with a Dean-Stark and the mixture was heated to reflux. As each 10 ml of azeotroping condensate was collected and removed, further aliquots of toluene (10 ml) were added to the reaction to maintain its volume. After one hour at reflux and the addition of three aliquots of toluene, the yellow suspension was cooled and filtered to give an intermediate enamine (0.19 g). This was added to a solution of hydroxylamine hydrochloride (0.05 g, 0.69 mmol) in a mixture of 5N sodium hydroxide (138 μl) and 70% aqueous acetic acid (676 μl). The reaction was stirred at room temperature for 10 mins, then THF (5 ml) was added and stirring was continued for 30 mins after which it was diluted with water (50 ml) and extracted twice with ethyl acetate (50 ml). The ethyl acetate phase was dried Na$_2$SO$_4$), evaporated and chromatographed on silica (eluting with ethyl acetate/hexane 1:2) and crystallised from ethyl acetate to give the product as a yellow solid (0.02 g, 11%) with m.p. 259°–260° C. (Found: C, 66.86; H, 4.97; N, 16.80. $C_{18}H_{16}N_4O_2$.0.1EtOAc requires: C, 67.14; H, 5.14; N, 17.02%); δH [$^2H_6$]-DMSO 11.64 (1H, s, 1-NH), 10.86 (1H, s, 5-NH), 10.63 (1H, s, OH), 9.91 (1H, d, J 9.5, =CHN$\underline{H}$), 8.14 (1H, d, J 7.5, 9-H), 7.88 (1H, s, 10-H), 7.75 (1H, d, J 9.5, =C$\underline{H}$NH), 7.47–7.32 (2H, m, 6-H 7-H), 7.13–7.04 (1H, m, 8-H), 2.95 and 2.93 (2×3H, 2×s, 3-CH$_3$ and 4-CH$_3$); m/z 321 (M$^+$).

Hydroxyaminomethylidene-(3,4-dimethylpyrrolo[3,2-b]carbazole-2-carboxamide) (0.404 g, 1.26 mmol) in a mixture of dioxane (30 ml) and glacial acetic acid (30 ml) was heated at reflux for five hours and then evaporated in vacuo. Chromatography on silica (eluting with ethyl acetate/hexane 1:3) gave the title compound as a yellow solid (0.008 g, 2%) with m.p. >250° C. (decomp.) δH [$^2H_6$]-DMSO 11.65 (1H, s, 1-NH), 10.61 (1H, s, 5-NH), 9.06 (1H, s, 3'-H), 8.09 (1H, d, J 7.5, 9-H), 7.92 (1H, s, 10-H), 7.45–7.34 (2H, m, 6-H, 7-H), 7.12–7.06 (1H, m, 8-H), 3.00 and 2.94 (2×3H, 2×s, 3-CH$_3$ and 4-CH$_3$); m/z (%) 302 (100, M$^+$), 260 (70), 232 (44); (Found: M$^+$, 302.11626. $C_{18}H_{14}N_4O$ requires 302.11676).

Assays for compound actiyity

Assays for cell proliferation/cytotoxicity were carried out in tissue culture grade 96 well microtitre plates (Costar). Cells in log growth were added to the plates at a concentration of $1 \times 10^3$ cells per well on day 0 and serially diluted compounds were then added on day 1. Plates were then incubated at 37° C. in 5% $CO_2$ in air for a further 4 days.

For quantitation of cell growth, the methylene blue biomass staining method was used, the test being read on a Multiscan plate reader at wavelength of 620 nm. The morphology of the cells was checked microscopically under phase-contrast immediately before fixation and staining with methylene blue, and by ordinary light microscopy thereafter. IC50 values for active compounds were obtained using the computer programme, GS1 and dose-response slopes were also plotted.

When compounds were tested for activity in a colony forming assay the methods used were identical to those described earlier except that serially diluted compound was added to the sloppy agar when the test was set up, and replenished at the same concentration on day 7. The test results were read on day 14.

Results

Comparative growth and morphology of HT1080scc2 and HT10801c

Growth rates in terms of cell number were similar for both lines to day 4 but thereafter HT1080scc2 cells continued to divide to reach saturation densities approximately 2 to 3 times higher than HT10801c by day 5.

Phenotypic differences between the 2 lines were clearly evident. HT10801c cells displayed a much flatter morphology than the transformed cells and only a few mitotic cells were seen in confluent areas of the cultures. HT1080scc2 cells however continued to divide with numerous mitotic cells visible after confluence.

Grown under anchorage independent conditions in soft agar, HT1080scc2 produced several large colonies whereas HT10801 cells failed to produce any colonies greater than 0.1 mm in diameter.

Effects of selected compounds

A number of compounds of the invention were evaluated against the cell lines. The compounds of the invention exhibited low toxicity with IC50 values in the range 50–100 $\mu$M.

The results of the "flattening" assay for compounds of the invention are shown below:

| Example | SCC2 Minimum flattening conc. (nM) |
|---------|-------------------------------------|
| 2       | 6                                   |
| 3       | 25                                  |

The compounds are effective at achieving "flattening" ie de-transformation, at levels significantly below their toxicity level.

We claim:
1. A compound of the formula (I)

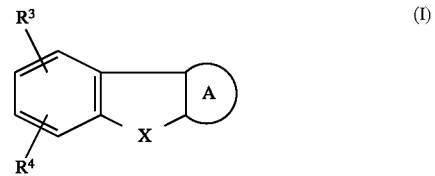

or a salt thereof, wherein
A) is

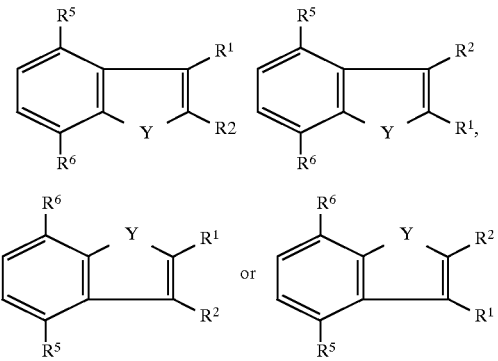

X is O, S, SO, $SO_2$, $CH_2$, CO or $NR^7$, wherein $R^7$ is H or the following groups which may be optionally substituted: cyloalkyl, cycloalkenyl, alkyl, alkenyl, alkynyl, aryl, aralkyl, acyl, aroyl, alkylsulphonyl or arylsulphonyl;

Y is O, S, SO, $SO_2$, $CH_2$, CO or $NR^7$;

$R^1$ is an optionally substituted 5- or 6-membered heterocyclic ring containing 1 to 4 heteroatoms wherein the 5- or 6- membered ring may be aromatic or non-aromatic;

$R^2$ is H, hydroxy, halo, haloalkyl, cyano, alkyl, aryl, alkenyl, alkynyl, alkoxy, wherein alkyl, aryl, alkenyl, alkynyl, and alkoxy may be substituted, CHO, $COR^8$, $COOR^8$ wherein $R^8$ is hydrogen or is a $C_{1-10}$ optionally substituted hydrocarbyl group which may contain one or two oxygen atoms;

$R^3$ and $R^4$ are independently H, hydroxy, alkyl, haloalkyl, azido, CHO, $COR^8$, $CO_2R^8$, $CONHR^8$, $CONR^8R^9$, alkoxy, halo, cyano, nitro, amino, alkyl amino, dialkyl amino, carboxyl wherein $R^9$ is alkyl, aryl or aralkyl;

$R^5$ is H, hydroxy, nitro, amino, halo, cyano, CHO, $COR^8$, or the following groups which may be optionally substituted: alkyl, aryl, aryloxy, aralkyloxy, alkoxy, aralkyl;

$R^6$ is H, hydroxy, amino, nitro, halo, CHO, $COR^{10}$, $CO_2R^{10}$ wherein $R^{10}$ is optionally substituted alkyl or aryl, or $R^6$ is alkyl, aralkyl, or aryl wherein alkyl, aralkyl or aryl may be optionally substituted.

2. A compound as claimed in claim 1 wherein
X is O, S, SO, $SO_2$,$CH_2$, CO or $NR^7$ wherein $R^7$ is H, alkyl, aralkyl, aryl, alkenyl, aryl, alkynyl or sulphonyl;

$R^1$ is an optionally substituted five or six-membered heterocyclic ring containing one or two nitrogen atoms and optionally one other heteroatom;

$R^2$ is H, alkyl or $COOR^8$ wherein $R^8$ is as defined in claim 1;

$R^3$ and $R^4$ are independently H, hydroxy, alkyl, haloalkyl, alkoxy, halo, cyano, nitro, amino, alkylamino, dialkylamino or substituted alkyl;

$R^5$ is H, alkyl, substituted alkyl, aryl, aralkyl, nitro, halo, cyano or CHO; and $R^6$ is H, alkyl, nitro, halo, CHO, or $COR^{10}$ wherein $R^{10}$ is alkyl or aryl or a salt thereof.

3. A compound as claimed in claim 2 wherein A is

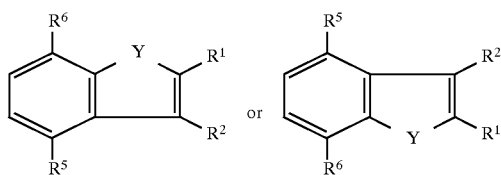

X is S or NH;

Y is NH;

$R^1$ is an optionally substituted five-membered ring containing two nitrogen atoms and one oxygen atom wherein the 5-membered ring may be aromatic or non-aromatic;

$R^2$ is H or $C_{1-4}$ alkyl;

$R^3$ is H, alkoxy, halo or hydroxy;

$R^4$ is H, alkoxy, halo or hydroxy;

$R^5$ is H or alkyl; and $R^6$ is H or alkyl or a salt thereof.

4. A compound as claimed in claim 1 which is 3,4-Dimethyl-2-(3-ethyl-1,2,4-oxadiazol-5-yl) pyrrolo[3,2-b]carbazole;

2-(3-Benzyl-1,2,4-oxadiazol-5-yl)-3,4-dimethylpyrrolo [3,2-b]carbazole;

3,4-Dimethyl-2-(3-ethyl-1,2,4-oxadiazol-5-yl) pyrrolo[2,3-b]carbazole;

2-(3-ethyl-1,2,4-oxadiazol-5-yl)-4-methyl-1H-[1] benzothieno[2,3ƒ]indole;

3,4-Dimethyl-2-(2-methyl-1,3,4-oxadiazol-5-yl)-pyrrolo [3,2-b]carbazole;

3,4-Dimethyl-2-(2-ethyl-1,3,4-oxadiazol-5-yl)-pyrrolo[3,2-b]carbazole;

3,4-Dimethyl-2-(2-phenyl-1,3,4-oxadiazol-5-yl)-pyrrolo [3,2-b]carbazole; or 2-(2-Ethyl-1,3,4-oxadiazol-5-yl)-4-methyl-1H-[1] benzothieno[2,3-ƒ]indole;

or a salt thereof.

5. A pharmaceutical composition comprising at least one compound of claim 1 together with one or more pharmaceutically acceptable carriers, diluents or excipients.

6. A process for the preparation of a compound of the formula (I) as defined in claim 1 which comprises (a) reaction of a compound of the formula (II)

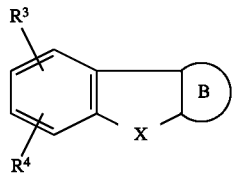

wherein

B) is

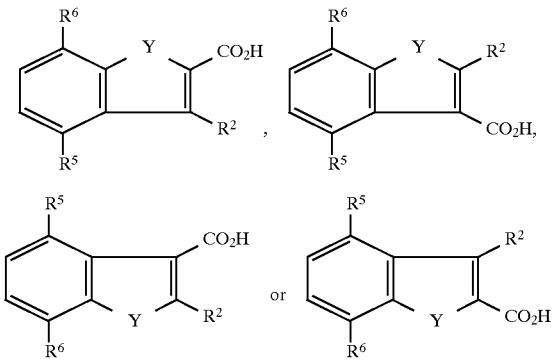

wherein X, Y, $R^2$, $R^3$, $R^4$, $R^5$ and $R^6$ are as defined above with the proviso that $R^3$, $R^4$, $R^5$ and $R^6$ are not $NH^2$ or $CO_2R^8$ and amines at $R^3$, $R^4$, $R^5$ and $R^6$ must be suitably protected and esters may be obtained by modification of an appropriate group at $R^3$, $R^4$, $R^5$ and $R^6$ after the oxadiazole is formed, with carbonyl diimidazole in tetrahydrofuran, followed by reaction with the required amidoximes pretreated with sodium hydride and molecular sieves, at a temperature between 0° C. and 150° C.; or (b) for compounds of the formula (I) wherein $R^1$ is a 1,3,4-oxadiazole ring by reaction of a compounds of the formula (IIa)

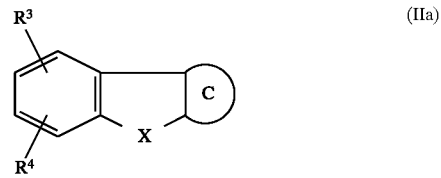

wherein

C) is

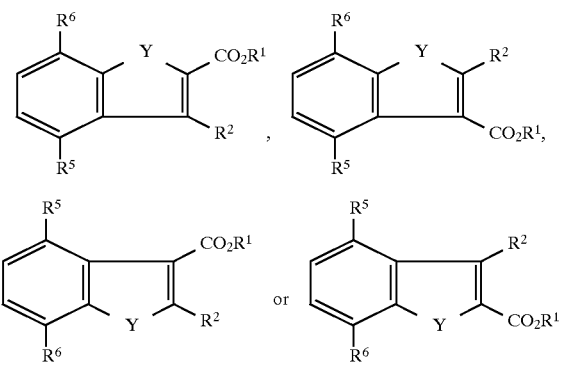

wherein X Y, $R^3$, $R^4$, $R^5$ and $R^6$ are as defined above with the proviso that $R^2$, $R^3$, $R^4$ and $R^5$ are not CHO, $COR^8$ or $CO_2R^8$ and $R^6$ is not CHO, $COR^{10}$ or $CO_2R^{10}$; Such groups may be introduced by formylation and subsequent modification after the oxadiazole is formed and $R^{11}$ is an alkyl group, with hydrazine hydrate to produce the hydrazide, this then being reacted with an ortho ester in a suitable solvent at a temperature between 0° C. and 150° C.;

(c) for compounds of the formula (I) wherein $R^1$ is 1,2,4-oxadiazole or a 1,3,4-oxadiazole ring by reaction of a compound of the formula (III) with a compound of the formula (IVa) in the presence of an acid catalyst;
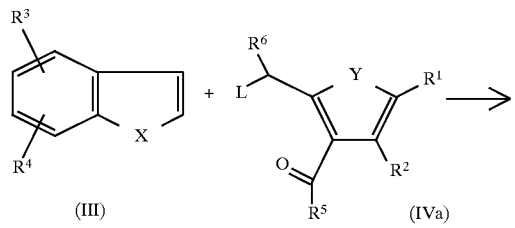
(III)   (IVa)
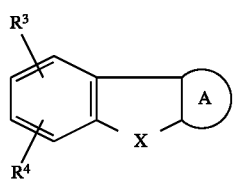
wherein
A) is
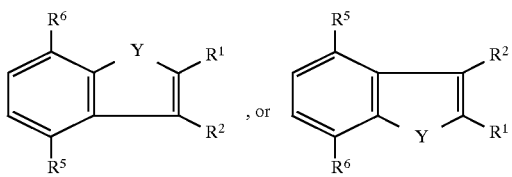
wherein X, Y, $R^1$, $R^2$, $R^3$, $R^4$, $R^5$, $R^6$ are defined above.
7. A method of treating a tumor comprising administering to a patient an effective amount of a compound of claim 1.
* * * * *